(12) United States Patent
Lorens et al.

(10) Patent No.: US 10,317,405 B2
(45) Date of Patent: Jun. 11, 2019

(54) METHODS OF DETECTING AKT3 AND ADMINISTERING AX1 INHIBITOR

(71) Applicant: BERGENBIO ASA, Bergen (NO)

(72) Inventors: Jim Lorens, Bergen (NO); Crina Tiron, Bergen (NO)

(73) Assignee: BERGENBIO ASA, Bergen (NO)

( * ) Notice: Subject to any disclaimer, the term of this patent is extended or adjusted under 35 U.S.C. 154(b) by 111 days.

(21) Appl. No.: 14/398,572

(22) PCT Filed: May 2, 2013

(86) PCT No.: PCT/IB2013/053488
§ 371 (c)(1),
(2) Date: Nov. 3, 2014

(87) PCT Pub. No.: WO2013/164788
PCT Pub. Date: Nov. 7, 2013

(65) Prior Publication Data
US 2015/0119475 A1   Apr. 30, 2015

Related U.S. Application Data

(60) Provisional application No. 61/641,512, filed on May 2, 2012.

(30) Foreign Application Priority Data

May 2, 2012 (GB) .................................. 1207722.8

(51) Int. Cl.
| G01N 33/53 | (2006.01) |
| G01N 33/573 | (2006.01) |
| G01N 33/50 | (2006.01) |
| G01N 33/574 | (2006.01) |
| A61K 38/45 | (2006.01) |
| A61K 45/06 | (2006.01) |

(52) U.S. Cl.
CPC .......... G01N 33/573 (2013.01); A61K 38/45 (2013.01); A61K 45/06 (2013.01); G01N 33/502 (2013.01); G01N 33/5073 (2013.01); G01N 33/574 (2013.01); G01N 33/57496 (2013.01); C12Y 207/11 (2013.01); G01N 2333/91205 (2013.01); G01N 2800/50 (2013.01)

(58) Field of Classification Search
None
See application file for complete search history.

(56) References Cited

U.S. PATENT DOCUMENTS

| 8,133,684 | B2 | 3/2012 | Aebersold et al. |
| 8,557,516 | B2 | 10/2013 | Mahajan et al. |
| 8,735,064 | B2 | 5/2014 | Micklem et al. |
| 2006/0062790 | A1 | 3/2006 | Reinhard |
| 2012/0003209 | A1 | 1/2012 | Tran |
| 2012/0021983 | A1 | 1/2012 | Tsichlis et al. |
| 2012/0028264 | A1 | 2/2012 | Shak et al. |
| 2012/0040842 | A1 | 2/2012 | Baker et al. |
| 2012/0159655 | A1 | 6/2012 | Lorens et al. |

FOREIGN PATENT DOCUMENTS

| CN | 102421919 | 4/2012 | |
| WO | WO 2004/086038 | 10/2004 | |
| WO | WO 2004/096135 | 11/2004 | |
| WO | WO 2008042867 A2 * | 4/2008 | ........... C07D 213/68 |
| WO | WO 2008/098139 | 8/2008 | |
| WO | WO 2010/083465 | 7/2010 | |
| WO | WO2010103388 | 9/2010 | |
| WO | WO 2010103388 A2 * | 9/2010 | ........... C12Q 1/6886 |
| WO | WO 2010/115119 | 10/2010 | |
| WO | WO 2010115119 A2 * | 10/2010 | ........... C12Q 1/6886 |
| WO | WO 2011/051392 | 5/2011 | |
| WO | WO 2012061510 A2 * | 5/2012 | ........... C12Q 1/6886 |

OTHER PUBLICATIONS

Holland et al (Cancer Res, 2010, 70(4): 1544-1554).*
Nakatani et al (JBC, 1999, 274(31): 21528-21532).*
Al-Saad, Samer, et al., "Diverse prognostic roles of Akt Isoforms, PTEN and PI3K in tumor epithelial cells and stromal compartment in non-small cell lung cancer," (2009) Anticancer Research 29:4175-4184.
Grabinski, N. et al., "Distinct functional roles of Akt isoforms for proliferation, survival, migration and EGF-mediated signalling in lung cancer derived disseminated tumor cells," (2011) Cellular Signalling, 23(12):1952-1960.
Hanrahan, A. J. et al., "Genomic complexity and AKT dependence in serous ovarian cancer," Cancer Discov. Jan. 1, 2012; 2(1): 56-67.
Lindsley C.W., "The Akt/PKB family of protein kinases: a review of small molecule inhibitors and progress towards target validation: a 2009 update," Curr Top Med Chem. 2010; 10:458-477.
Nakatani, K. et al., "Up-regulation of Akt3 in estrogen receptor-deficient breast cancers and androgen-independent prostate cancer lines," (1999) J. Biological Chem. 274(31):21528-21532.
Stahl, J.M. et al., "Deregulated Akt3 activity promotes development of malignant melanoma," (2004) Cancer Research 64(19):7002-7010.
Tuomi, S. et al., "PKCepsilon regulation of an alpha5 integrin-ZO-1 complex controls lamellae formation in migrating cancer cells," 2009 Sci Signal 2(77):ra32.
International Search Report and Written Opinion for International Patent Application No. PCT/IB2013/053488 dated Oct. 29, 2013.

(Continued)

*Primary Examiner* — Sean E Aeder
(74) *Attorney, Agent, or Firm* — Quarles & Brady LLP

(57) ABSTRACT

The use of Akt3 as a biomarker for detecting the occurrence of epithelial-to-mesenchymal transition (EMT) in a subject, and the use of Akt3 inhibitors to treat cancer is disclosed herein. Also disclosed are various methods for detecting the occurrence of epithelial-to-mesenchymal transition (EMT) in a subject by measuring Akt3 expression and/or activity.

14 Claims, 23 Drawing Sheets
Specification includes a Sequence Listing.

(56) References Cited

OTHER PUBLICATIONS

Bellacosa, A., Larue, L., et al, PI3K/AKT Pathway and the Epithelial-Mesenchymal Transition, 2010, Cancer Genome and Tumor Microenvironment, 11-32.

Cristiano, B., et al, A Specific Role for AKT3 in the Genesis of Ovarian Cancer through Modulation of $G_2$-M Phase Transition, 2006, Cancer Res, vol. 66: 17718-17725.

Dubrovska, A., et al, The Role of PTEN/Akt/PI3K signaling in the maintenance and viability of prostate cancer stem-like cell populations, 2008, PNAS, vol. 106: 106, 268-273.

Eyler, C, et al, Brain Cancer Stem Cells Display Preferential Sensitivity to Akt Inhibition, 2008, Stem Cells, vol. 26: 3027-3036.

Grille, et al, The protein kinase Akt induces epithelial mesenchymal transition and promotes enhanced motility and invasiveness of squamous cell carcinoma lines, 2003, Cancer Research, vol. 63: 2172-2178.

Hambardzumyan, D, et al, PI3K pathway regulates survival of cancer stem cells residing in the perivascular niche following radiation in medulloblastoma in vivo, 2008, Genes and Development, vol. 22: 436-448.

Larue, L., Bellacosa, A., Epithelial-mesenchymal transition in development and cancer: role of phosphatidylinositol 3' kinase/AKT pathways, 2005, Oncogene, vol. 24: 7443-7454.

Lepage, C., et al, Expression and localization of Akt-1, Akt-2 and Ak-t3 correlate with clinical outcome of prostate cancer patients, 2006, British Journal of Cancer, vol. 94: 1906-1912.

Madhunapantula, S, The PTEN-AKT Signaling Cascade as a Therapeutic Target in Melanoma, 2009, Pigment Cell Melanoma Res, 400-419.

Ruan, G-X., Axl is essential for VEGF-A-dependent activation of PI3K/Akt, 2012, Embo Journal, 31: 1692-1703.

Singh, Anurag and Settleman, Jeffrey, EMT, cancer stem cells and drug resistance: an emerging axis of evil in the war on cancer, Oncogene, 2010, 29(34), pp. 4741-4751.

Thiery, Jean Paul, et al., Epithelial-Mesenchymal Transitions in Development and Disease, Cell, 2009, 139, pp. 871-890.

Zeisberg, Michael and Neilson, Eric G., Biomarkers for epithelial-mesenchymal transitions, J Clin. Invest., 2009, 119, pp. 1429-1437.

* cited by examiner

Figure 13

| Cells injected | Tumor incidence | | | |
|---|---|---|---|---|
| | $10^6$ | $10^5$ | $10^4$ | $10^3$ |
| HMLER/vector | 5/10 | 6/10 | 4/10 | 1/10 |
| HMLER/myrAkt1 | 6/10 | 6/10 | 3/10 | 0/10 |
| HMLER/myrAkt3 | 10/10 | 10/10 | 10/10 | 10/10 |

METHODS OF DETECTING AKT3 AND ADMINISTERING AX1 INHIBITOR

CROSS-REFERENCE TO RELATED APPLICATIONS

This patent application is a national stage filing under 35 U.S.C. 371 of International Application No. PCT/IB013/053488, filed May 2, 2013, which claims the benefit of priority of Great Britain Application No. GB1207722.8, filed May 2, 2012 and of United States Provisional Patent Application No. 61/641,512, filed May 2, 2012, all of which are incorporated herein by reference in their entireties.

FIELD OF INVENTION

This invention relates to the fields of drug development and cancer treatment. In particular this invention relates to the field of protein kinases and more particularly to methods of prognosing and treating cancer.

BACKGROUND TO THE INVENTION

Akt

Akt (Protein kinase B) is a serine/threonine protein kinase that is known to be involved in diverse cellular processes including proliferation, motility, growth, glucose homeostasis, survival and cell death. Akt is one of the three principal components of the PI3K/Akt pathway (phosphatdylinositol 3-kinase, its antagonist PTEN and Akt). Mutation in components of this pathway are among the most frequently observed mutations in cancers and are found in up to 70% of breast cancers. In humans, there are three Akt family members, Akt 1, Akt 2 and Akt3 which are transcribed from different genes. The majority of research publications on Akt refer either to Akt1 or to Akt without specifying which family member, a consequence of the widespread use of pan-Akt antibodies that do not distinguish between the family members. Of the three isoforms, least is known about Akt3. Indeed, in a recent review article "Key signalling nodes in mammary gland development and cancer. Signalling downstream of PI3 kinase in mammary epithelium: a play in 3 Akts" (Wickenden J A and Watson C J, Breast Cancer Research 2010, 12, 202), Akt3 is mentioned just three times: once to establish its existence, once to note that it appears to have a minor role in normal mammary gland development and once to note that it does not affect Stat5a phosphorylation during pregnancy and lactation.

The roles for Akt1, Akt2 and Akt3 in normal development have been studied in knock-out mice, revealing that Akt1 is important for overall growth (knock-out mice are generally healthy but have reduced growth). Akt2 is primarily involved in glucose metabolism (knockout mice grow normally but show insulin resistance) and Akt3 is important in brain development (see e.g. Dummler B, Hemmings B A. Physiological roles of PKB/Akt isoforms in development and disease. Biochem Soc Trans 2007; 35:231-5). A more general role for Akt1 and Akt2 is suggested by their widespread expression throughout the body, while Akt3 has more restricted expression in the brain, kidney and heart.

Akt is considered an attractive target for cancer therapy, and inhibition of Akt alone or in combination with standard cancer chemotherapeutics has been postulated to reduce the apoptotic threshold and preferentially kill cancer cells (Lindley C W, Curr Top Med Chem, 10, 458, 2010). A recent review of attempts to inhibit Akt members pinpoints Akt2 as the most commonly mutated family member in cancers and suggests that inhibition of Akt1 and Akt2 would be optimal (Mattmann M E at al "Inhibition of Akt with small molecules and biologics: historical perspective and current status of the patent landscape", Expert Opinion on Therapeutic Patents, 21, 1309, 2011). Many of the compounds covered in this review have poor selectivity for Akt compared to other kinases and generally focus on Akt1. Compounds reported in this review with selectivity between the different family members overwhelmingly inhibit Akt1 and/or Akt2 rather than Akt3.

Despite the overwhelming focus on Akt1 in the literature, Akt3 overexpression has been linked to several cancers including melanoma (Cancer Res. 2004 Oct. 1; 64(19):7002-10) and ovarian cancer (Cancer Discov. 2012 Jan. 1; 2(1): 56-67).

Several patent publications relate to the use of Akt3.

WO2010/091354 (H Lee Moffat Cancer Institute, Inc.) relates to methods of diagnosing cancer in a subject involving determining levels of expression of Tyrosine 176-phosphorylated AKT1 rather than AKT3.

US20120040842 (Baker, at al.) lists Akt3 amongst a vast array of genes that may be assessed to determine the prognosis of colorectal cancer. However, Akt3 is not selected as a preferred marker.

US20120028264 (Shag, at al.) lists Akt3 {Table 3A} amongst a vast any of genes, expression levels of which may be determined in the assessing the likelihood of prostate cancer recurring in a subject. The significance of Akt3 is not specifically mentioned.

US20120021983 (Tsichlis, et al.) relates to a method of diagnosing or prognosing a potential cancer and progression of an existing cancer by assessing a subject's Akt isoform profile, especially the ratio of Akt1 to Akt2, by comparing that profile with a normal Akt isoform profile.

US20120003209 (The Translational Genomics Research Institute) relates to methods and kits used in the identification of invasive glioblastoma based upon the expression levels of Akt1 and Akt2. Akt3 mRNA expression was found to be high in non-neoplastic brain speciments and decreased in glial tumours. Furthermore Akt3 expression was found to be significantly higher in long term surviving patients.

U.S. Pat. No. 8,133,684 (Aebersold et al.) discloses methods of determining androgen responses in prostate cells, mentioning Akt3 in a long list of possible prostate cancer biomarkers.

The Epithelial-Mesenchymal Transition (EMT)

Epithelial tissues make up one of the four basic tissue types of the body, along with connective tissue, muscle and nervous tissue. Epithelial cells are characterised by a tendency to form into sheets of polarised cells held together by strong intercellular junctions. As a consequence of this, epithelial cells are not able to move freely and show little migration compared to other cell types. In contrast, mesenchymal-like cells (e.g. fibroblasts) lack strong intercellular junctions and can move as individual cells. They can be highly motile and able to migrate through the extracellular matrix.

The Epithelial-Mesenchymal Transition (EMT) is a natural cellular program in which individual epithelial cells lose the gene expression patterns and behaviours characteristic of epithelial cells and instead begin to look, behave and express genes typical of mesenchymal cells. In so doing they lose adhesion and apical-basal polarity and gain the ability to migrate and invade the extracellular matrix. EMT is not irreversible. A mirror process called Mesenchymal-Epithelial Transition (MET) results in the loss of mesenchymal characteristics and re-establishment of cell-cell adhesion and apical-basal polarity.

EMT is especially important during embryonic development. It plays a fundamental role in gastrulation, where an embryo consisting of a single epithelial cell layer develops into one with the three classical germ layers, ectoderm, mesoderm and endoderm. Slightly later in vertebrate development, EMT gives rise to the neural crest cells. These cells migrate throughout the embryo and give rise to many different structures including ganglia of the peripheral nervous system, bone and cartilage of the face and head, pigment cells and glial cells. Further rounds of MET and EMT are essential for the formation of internal organs from both the mesoderm and endoderm.

EMT and Disease

In contrast to its importance during embryonic development, the EMT program is seldom activated in healthy adults. It is, however, induced in response to inflammation following injury or disease: EMT plays a role in wound healing and tissue repair, and occurs during organ degenerative disease (e.g. renal fibrosis).

EMT is also increasingly understood to play a key role in cancer metastasis. Carcinomas are epithelial cancers, and, in order for metastasis to occur, individual cells must escape the primary tumour and undergo a series of migrations. These include migration from the primary tumour into the local circulatory or lymphatic system, and extravasation from the vasculature and establishment at the site of metastasis. There is now good and growing evidence that interactions between tumour cells and their microenvironment can lead to induction of EMT in some of the tumour cells. The resulting increased cell migration and invasion potential of these cells then enhances the likelihood of a metastasis becoming, established. The receptor tyrosin kinase Axl, which is a chronic myelogenous leukemia-associated oncogene, has recently been shown to be an essential EMT-induced effector in the invasion metastasis cascade (WO2010/103388).

As well as this role in increasing metastatic potential, the EMT program has recently been linked with Cancer Stein Cells (CSCs). These cells have been postulated to represent a subset of tumour cells with stem cell characteristics—i.e. the ability to give rise to all the cell types found in a particular cancer, and thus the ability to form a new tumour. Although they may represent only a tiny fraction of the cells in a tumour, CSCs are thought to be particularly resistant to existing anti-cancer drugs. Even though drug treatment may kill the vast majority of cells in the tumour, a single surviving CSC can therefore lead to a relapse of the disease. Recent evidence suggests an overlap between EMT and CSC phenotypes, suggesting that EMT may also play a role in recurrence of cancer after chemotherapy and the development of drug-resistant tumours.

Robust biomarkers for the EMT phenotype would be useful in identifying patients at particular risk of developing metastatic or drug-resistant cancer, while novel drugs that target cells that have undergone EMT will reduce metastasis and relapse following conventional therapy.

EMT activators (e.g. the transcription factor Slug) increase Akt1 activity/expression. It is also known that Akt1 activation (for example of the myristylated variant MyrAkt1) induces EMT activators (e.g. the transcriptional repressor, Snail; Oncogene. 2007 Nov. 22; 26(53):7445-56. Epub 2007 Jun. 1) and also causes biomarker switching from epithelial to mesenchymal.

SUMMARY OF THE INVENTION

Unexpectedly it has now been found that Akt3 plays a central role in the induction of EMT and cancer stem cell traits in human cells. In particular, it has been found that constitutively active Akt3 significantly increases the ability of cells to form tumours in vivo and mammospheres, compared to control cells or cells expressing constitutively active Akt1. Further, inhibition of Akt3 was able to reverse EMT and CSC traits.

This was unexpected in view of the focus in the field on Akt1 and Akt2.

It has also been found that Akt3 is a biomarker for Axl receptor tyrosine kinase signalling. More specifically Akt3 has been shown to be a biomarker for Axl signalling in epithelial cells. Akt3 has also been found to participate in a feedback loop leading to maintenance of EMT. Further applications of Akt3, such as a biomarker of cancer stem cells, metastasis will be apparent from this disclosure.

According to one aspect of the invention, there is provided a method of selecting a pharmaceutical compound useful for the prevention, inhibition or treatment of an Akt3-related condition, the method comprising providing a group of candidate pharmaceutical compounds for testing, testing the effect of candidate pharmaceutical compounds on Akt3 activity in a test system, and selecting a candidate pharmaceutical compound on the basis of inhibiting Akt3 activity.

Alternatively the invention provides a method of selecting a candidate pharmaceutical compound useful in the treatment of metastatic or drug resistant cancer, the method comprising providing a group of candidate pharmaceutical compounds for testing, testing the effect of candidate pharmaceutical compounds on Akt3 activity in a test system, and selecting a candidate pharmaceutical compound on the basis of its inhibition of Akt3 activity.

According to another aspect there is provided a method of selecting a candidate pharmaceutical compound useful in the prevention or inhibition of EMT, the method comprising providing a group of candidate pharmaceutical compounds for testing, testing the effect of candidate pharmaceutical compounds on Akt3 activity in a test system, and selecting a candidate pharmaceutical compound on the basis of inhibiting Akt3 activity.

It is highly advantageous to be able to determine effective levels of a candidate pharmaceutical compound in an in vitro test system in order to predict in vivo responses. This facilitates determination of effective minimum dosage levels of a pharmaceutical compound and also the validation of drug targets in a dose-dependent manner. A particularly useful approach to predicting in vivo responses to a pharmaceutical is through conditional selective knockout of a target gene through RNA interference. The effective generation of nucleotides for use in such methods is described in WO2009/082488.

According to another aspect of the invention there is provided a method of selecting a candidate pharmaceutical compound useful in the prevention, inhibition or treatment of an Akt3-related condition, the method comprising selectively reducing expression of Akt3 in a test cell, contacting the test cell with the candidate pharmaceutical compound and determining the effect of the candidate pharmaceutical compound on inhibition of Akt3 activity.

According to a further aspect of the invention there is provided a method of selecting a compound useful in the prevention, inhibition or treatment of an Akt3-related condition, the method comprising selectively reducing expression of Akt3 in an in vitro test system to a low level contacting the test system with a candidate pharmaceutical compound, and selecting candidate pharmaceutical compounds which inhibit Akt3 activity.

According to a further aspect of the invention there is provided a method of identifying a subject having an Akt3-related condition, the method comprising assessing the level of expression or activity of Akt3 in the subject, or in a sample derived from the subject. Generally, the level of expression or activity in a subject or in a sample derived from a subject may be determined relative to a control sample, as described herein.

According to a further aspect of the invention there is provided a method of identifying a subject having a particular risk of developing metastatic or drug-resistant cancer, the method comprising assessing the level of expression or activity of Akt3 in the subject, or in a sample derived from the subject, an increased level of Akt3 expression or activity indicating an increased risk of the subject of developing metastatic or drug-resistant cancer.

According to a further aspect of the invention there is provided a method of identifying the presence of a Cancer Stem Cell in a subject, the method comprising determining the level of Akt3 expression or activity in the subject, or in a sample derived from the subject, increased expression or activity of Akt3 indicating the existence of a Cancer Stem Cell (CSC).

According to a further aspect of the invention there is provided a method of identifying a subject undergoing EMT, the method comprising determining the level of Akt3 expression or activity in the subject, or in a sample derived from the subject, an increase in expression or activity of Akt3 indicating the occurrence of EMT.

According to a further aspect of the invention there is provided a method of prognosing a cancer-related outcome in a subject, the method comprising assessing Akt3 activity or expression in the subject, or in a sample derived from the subject. In some embodiments, an increase in Akt3 activity or expression relative to a control sample is indicative of susceptibility to treatment with a cancer therapeutic agent, for example an capable of inhibiting or reversing EMT. The agent may be as described herein, e.g. an Akt3 inhibitor or an Axl inhibitor.

According to a further aspect of the invention there is provided a method of identifying Axl activity, the method comprising determining the level of Akt3 expression or activity in the subject, or in a sample derived from the subject, increased activity or expression of Akt3 correlating with Axl activity.

It has unexpectedly been found that the level of expression or activity of Akt3 is inversely correlated with the level of expression or activity of Akt2. The methods and uses of the invention comprise assessing the level of expression or activity of Akt2 in a subject or in a sample derived from the subject. A decreased level of Akt2 expression or activity may indicate: (i) the subject has an Akt3-related condition; (ii) an increased risk of the developing metastatic or drug-resistant cancer; (iii) the existence of a cancer stem cell; and/or (iv) the occurrence of EMT.

In some embodiments, the level of expression or activity of both Akt2 and Akt3 is assessed. Assessing two inversely correlated biomarkers may increase assay reliability.

In some embodiments, the level of expression of Akt3 is assessed by determining the copy number of the gene encoding Akt3 relative to a control sample, wherein an increase in the copy number indicates an increased level of expression of Akt3. Copy number (i.e. gene duplication events) may be determined using standard techniques known in the art, e.g. using a DNA chip as described in Jiang et al. (Jiang Q, Ho Y Y, Hao L. Nichols Berrios C, Chakravarti A. Copy number variants in candidate genes are genetic modifiers of Hirschsprung disease. PLoS One. 2011; 6(6)).

In some embodiments, wherein the level of expression of Akt3 (or Akt2) is assessed by determining the level of Akt3 (or Akt2) protein or mRNA. Methods for determining protein and mRNA expression levels are well known in the art, and described herein.

In some embodiments, Akt3 activity is assessed by determining phosphorylation of Akt3, wherein phosphorylation of Akt3 indicates active Akt3. Akt3 phosphorylation may be determined at Serine 472, as described herein. Alternatively or additionally, phospholation may be determined at threonine 305 and/or tyrosine 174. This numbering refers to the Akt3 sequence; the corresponding Akt1 residues are S473, T308 and Y176, respectively Without being limited, by theory, it is believed that phosphorylation at threonine 305 is important in localization of Akt3 to the nucleus, leading to phosphorylation at tyrosine 174 and serine 472 and activation of Akt3. In some embodiments, Akt3 activity is assessed by determining the intracellular localisation of Akt3 protein, wherein localisation in the nucleus indicates active Akt3.

In some embodiments, Akt3 activity is assessed by determining the expression levels of downstream targets, for example genes associated with EMT. In further embodiments, Akt3 kinase activity may be assessed by determining phosphorylation of substrate proteins (e.g. SNAIL) or peptides, for example as described in Tuomi et al., 2009 (Sci Signal. 2009 Jun. 30 2(77)).

According to another aspect of the invention there is provided a method of treating a subject having an Akt3-related condition, the method comprising contacting the subject with an Akt3 inhibitor, or with a pharmaceutical compound selected as, or derived from, a candidate compound obtained by a method according to the first aspect of the invention.

Further aspects of the invention include a method of inhibiting EMT as subject, the method comprising contacting the subject with a compound capable of inhibiting Akt3 activity.

A further aspect of the invention provides a method of inhibiting Cancer Stem Cells in a subject, the method comprising of contacting the subject with a compound capable of inhibiting Akt3 activity, The invention also provides a method of preventing or inhibiting drag resistance in a subject having cancer, the method comprising contacting the subject with a compound capable of inhibiting Akt3 activity.

The invention also provides the use of an Akt3 inhibitor in the treatment of an Akt3 related condition, such as cancer.

The invention also provides the use of an Akt3 inhibitor in the inhibition of EMT.

The invention also provides an Akt3 inhibitor for use in a method of treatment as described herein.

According to a further aspect of the invention there is provided the use of a compound capable of inhibiting Akt3 activity in the prevention, inhibition, or treatment of drug resistance in a subject having cancer, the method comprising contacting the subject with a compound capable of inhibiting Akt3 activity.

Akt3 inhibitors identified by methods in accordance with the invention or used in methods or uses in accordance with the invention may be used as a monotherapy or in combination therapy with other cancer treatments as mentioned below.

Suitable chemotherapeutic agents include;

alkylating agents, including alkyl sulfonates such as busulfan;

nitrogen mustards such as chlorambucil, cyclophosphamide, estramustine, ifosfamide, mechlorethamine, melphalan, and uramustine, ethyleneimine derivatives such as thiotepa;

nitrosoureas such as carmustine, lomustine, and streptozocin, triazenes such as dacarbazine, procarbazine, and temozolamide, and platinum compounds such as cisplatin, carboplatin, oxaliplatin, satraplatin, and picoplatin ormaplatin, tetraplatin, sprioplatin, iproplatin, chloro(diethylenediamino)-platinum (II) chloride, dichloro(ethylenediamino)-platinum (II), diammo(2-ethylmalonato)platinum (II), (1,2-diaminocyclohexane)malonatoplatinum (II), (4-carboxyphthalo)-(1,2-diaminocyclohexane)platinum (II), (1,2-diaminocyclohexane)-(isocitrato)platinum (II), and (1,2-diaminocyclohexane)-cis-(pyruvato)platinum (II);

antimetabelites, including antifolates such as methotrexate, permetrexed, raltitrexed, and trimetrexate, pyrimidine analogs such as azacitidine, capecitabine, cytarabine, edatrexate, floxuridine, fluorouraca, gemeitabine, and troxacitabine, and purine analogs such as cladribine, chlorodeoxyadenosine, clofarabine, fludarabine, mercaptopurine, pentostatin, and thioguanine;

natural products, including antitumor antibiotics such as bleomycin, dactinomycin, mithramycin, mitomycin, mitoxantrone, porfiromycin, and anthracyclines such as daunorubicin, doxorubicin, epirubicin, idarubicin, and valrubicin, mitotic inhibitors such as the vinca alkaloids vinblastine, vinvesir, vincristine, vindesine, and vinorelbine, enzymes such as L-asparaginase and PEG-L-asparaginase, microtubule polymer stabilizers such as the taxanes paclitaxel and docetaxel, topisomerase I inhibitors such as the camptothecins irinotecan and topotecan, and topoisomerase II inhibitors such as podophyllotoxin, amsacrine, etoposide, teniposide, losoxantrone and actinomycin;

hormones and hormone antagonists, including androgens such as fluoxymesterone and testolactone, antiandrogens such as bicalutamide, cyproterone, flutamide, and nilutamide, corticosteroids such as dexamethasone and prednisone, aromatase inhibitors such as aminoglutethimide, anastrozole, exemestane, formestane, and letrozole, estrogens such as diethylstilbestrol, antiestrogens such as fulvestrant, raloxifene, tamoxifen, and toremifine, luteinising hormone-releasing hormone (LHRH) agonists and antagonists such as abarelix, buserelin, goserelin, leuprolide, histrelin, desorelin, nafarelin acetate and triptorelin, progestins such as medroxyprogesterone acetate and megestrol acetate, and thyroid hormones such as levothyroxine and liothyronine;

PKB pathway inhibitors, including perifosine, enzastaurin hydrochloride, and triciribine, P13K inhibitors such as semaphore and SF1126, and MTOR inhibitors such as rapamycin and analogues;

CDK inhibitors, including seliciclib, alvocidib, and 7-hydroxystaurosporine;

COX-2 inhibitors, including celecoxib;

HDAC inhibitiors, including trichostatin A, suberoylanilide hydroxamic acid, and chlamydocin;

DNA methylase inhibitors, including temozolomide; and miscellaneous agents, including altretamine, arsenic trioxide, thalidomide, lenalidomide, gallium nitrate, levamisole, mitotane, hydroxyurea, octreotide, procarbazine, suramin, photodynamic compounds such as methoxsalen and sodium porfimer, and proteasome inhibitors such as bortezomib.

Molecular targeted therapy agents including:

functional therapeutic agents, including gene therapy agents, antisense therapy agents, tyrosine kinase inhibitors such as erlotinib hydrochloride, gelitinib, imatinib mesylate, and semaxanib, Raf inhibitors such as sorafenib, and gene expression modulators such as the retinoids and rexinoids, for example adapalene, bexarotene, trans-retinoic acid, 9-cis-retinoic acid, and N-(4-hydroxyphenyl)retinamide; and phenotype-directed therapy agents, including monoclonal antibodies such as alemtuzumab, bevacizumab, cetuximab, ibritumornab tiuxetan, rituximab, and trastuzumab, immunotoxins such as gemtuzumab ozogamicin, radioimmunoconjugates such as 1-tositumobab, and cancer vaccines.

Biologic therapy agents including:

interferons such as interferon-[alpha]2a and interferon-[alpha]2b, and interleukins such as aldesleukin, denileukin diftitox, and oprelvekin. Axl inhibiting agents including 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine (BGB324/R428), CH5451098 (Roche) and Axl inhibitors described in PCT/US07/089177, PCT/US2010/021275 and PCT/EP2011/004451, incorporated herein by reference.

In addition to these agents intended to act against cancer cells, anticancer therapies include the use of protective or adjunctive agents, including:

cytoprotective agents such as amifostine, and dexrazoxane, phosphonates such as pamidronate and zoledronic acid, and stimulating factors such as epoetin, darbeopetin, filgrastim, PEG-filgrastim, and sargramostim.

Many combination chemotherapeutic regimens are known to the art, such as combinations of carboplatin/paclitaxel, capecitabine/docetaxel, fluorauracil/levamisole, fluorauracil/leucovorin, methotrexate/leucovorin, and trastuzumab/paclitaxel, alone or in further combination with carboplatin, and the like.

According to a further aspect of the invention is provided a method of selecting patients, preferably human patients, for treatment of an Akt3-related condition, the method comprising identifying patients having elevated Akt3 activity or expression and selecting thus identified patients for treatment. Patients may be identified according to the methods of the invention as described herein.

Preferably the Akt3-related condition is cancer. The cancer may be one or more of the following cancers: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheoehromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; genital cancers such as penile cancer; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. Preferably, the cancer is selected from breast, melanoma, prostate, ovarian, colorectal, lung or glioma cancer. More preferably the cancer is metastatic breast cancer.

The treatment of metastatic cancer depends on where the primary tumor is located. When breast cancer spreads to the lungs, for example, it remains a breast cancer and the treatment is determined by the metastatic cancer origin within the breast, not by the fact that it is now in the lung. About 5 percent of the time, metastatic cancer is discovered but the primary tumor cannot be identified. The treatment of these metastatic cancers is dictated by their location rather than their origin. Metastatic cancers are named by the tissue of the original tumor (if known). For example, a breast cancer that has spread to the brain is called metastatic breast cancer to the brain. Patients identified or selected according to the methods of the invention may be treated, or selected for treatment. For example, if Akt3 expression is shown to be upregulated in a primary tumor, this can be used to infer an increased probability of metastasis. This information can be used as a guide to treatment options, i.e. more aggressive anti-cancer surgical, chemotherapeutic or radiotherapeutic treatment such as radical mastectomy. In some embodiments, treatment comprises administration of an Akt3 and/or Axl inhibitor, optionally in combination with a further therapeutic agent described herein or known in the art. Preferably the Axl inhibitor is BGB324/R428.

The invention also provides cell lines which are sensitive to inhibitors to EMT, the cell line having a level of Akt3 expression that is insufficient to prevent EMT. Preferably the cell lines are human cell lines.

The invention also provides a method of identifying a compound which inhibits Akt3 activity, a method comprising contacting a cell from a cell line according to the invention with a test compound and determining inhibition of Akt3 activity in the cell.

One aspect of the invention relates to the use of Akt3 as a biomarker for detecting the occurrence of epithelial-to-mesenchymal transition (EMT) in a subject. In some embodiments, an increase in the expression and/or activation of Akt3 is indicative of the occurrence of epithelial-to-mesenchymal transition (EMT).

Metastasis to distant sites is the most common cause of death from solid tumors (Gupta 2006, Sporn 1996). To accomplish this, tumor cells discard epithelial restraints, redefine junctional complexes and acquire invasive motility to break across the basement membrane border. These metastatic cells then intravasate into the lymphatic and hematogenous circulation, disseminating to distant sites in the body. A few of these metastatic cells succeed in extravasating through the capillary wall and in rare cases colonize the foreign tissue stroma (Weinberg et al). This malignant process is facilitated by an epithelial-to-mesenchymal transition (EMT), a developmental program where epithelial cells transiently assume a mesenchymal phenotype during gastrulation and organogenesis, allowing single cell invasive movement away from the epithelial layer (Hall, 1985; Thierry, 2002). The EMT program is initiated by contextual activation of morphogen signaling pathways that induce the expression of transcriptional regulators, including Twist, Snail, Slug and Zeb2, which alter the expression of junctional complex proteins (Thiery and SLeeman 2006). The EMT gene expression profile reflects the phenotypic shift, repression of E-cadherin and cytokeratins with induction of vimentin and N-cadherin (Weinberg et al 2007).

The term "marker" or "biomarker" is used herein to refer to a gene or protein whose expression in a sample derived from a cell or mammal is altered or modulated, for example, up or down regulated, when epithelial-to-mesenchymal transition (EMT) takes place. Where the biomarker is a protein, modulation or alteration of expression encompasses modulation through different post translational modifications.

Post translational modifications are covalent processing events that change the properties of a protein by proteolytic cleavage or by addition of a modifying group to one or more amino acids. Common post translational modifications include phosphorylation, acetylation, methylation, acylation, glycosylation, GPI anchor, ubiquitination and so forth. A review of such modifications and methods for detection may be found in Mann et al. *Nature Biotechnology* March 2003, *Vol.* 21, *pages* 255-261.

Also provided herein is the use of Akt3 as a biomarker for detecting the expression and/or activation of Axl, wherein an increase in the expression and/or activation of Akt3 is indicative of an increase in the expression and/or activation of Axl.

The term "expression" refers to the transcription of a gene's DNA template to produce the corresponding mRNA and translation of this mRNA to produce the corresponding gene product (i.e., a peptide, polypeptide, or protein) as well as the "expression" of a protein in one or more forms that may have been modified post translation.

Detection of the level of expression including gene expression may be performed by any one of the methods known in the art, particularly by microarray analysis, Western blotting or by PCR techniques such as QPCR. Altered expression may also be detected by analysing protein content of samples using methods such as ELISA, PET or SELDI-TOF MS as described herein and using further analytical techniques such as 2Dgel electrophoresis. Techniques such as this can be particularly useful for detecting altered expression in the form of alternative post translationally modified forms of a protein.

Suitable samples include, but are not limited to, tissue samples such as biopsy, blood, urine, buccal scrapes etc, serum, plasma or tissue culture supernatant samples. In one embodiment, gene expression is preferably detected in tumour cells, particularly cells derived from a tumour such as breast, lung, gastric, head and neck, colorectal, renal, pancreatic, uterine, hepatic, bladder, endometrial and prostate cancers and leukemias or from blood cells such as lymphocytes and, preferably, peripheral lymphocytes such as PBMC.

In detection of proteins in serum and, in particular, in plasma samples of patients, samples are removed and subjected to protein analytical techniques such as flow cytometry, ELISA, PET and SELDI-TOF MS, as described herein.

In one preferred embodiment, the method comprises extracting RNA from said sample and detecting gene expression by QPCR.

In one embodiment, gene expression is detected by detecting protein products such as, for example, by Western Blot.

A further aspect of the invention provides a method for detecting the occurrence of epithelial-to-mesenchymal transition (EMT) in a sample, said method comprising determining the expression level or activation of Akt3 in a sample isolated from a cell, group of cells, an animal model or human as compared to a control sample, wherein an increase in the expression level or activation of Akt3 relative to the control sample is indicative of the occurrence of epithelial-to-mesenchymal transition (EMT).

A further aspect of the invention relates to a method for identifying an agent capable of inhibiting or reversing epithelial-to-mesenchymal transition (EMT), said method comprising administering said agent to as cell, group of cells or animal model, and monitoring the activation and/or the expression of Akt3.

In one embodiment, the method comprises:

(i) administering the agent to a cell, group of cells or an animal model, not a human; and (ii) measuring Akt3 expression and/or Akt3 activation in samples derived from the treated and the untreated cells or animal model; and (iii) detecting an increase in the expression and/or activation of Akt3 in the treated sample as compared to the untreated sample as an indication of the ability to inhibit or reverse epithelial-to-mesenchymal transition (EMT).

In some embodiments, the animal model is not a human.

In some embodiments, the level of expression of Akt3 is assessed by determining the copy number of the gene encoding Akt3 relative to a control sample, wherein an increase in the copy number indicates an increased level of expression of Akt3.

In some embodiments, the level of expression of Akt3 is assessed by determining the level of Akt3 protein or mRNA.

In some embodiments. Akt3 activity is assessed by determining phosphorylation of Akt3, wherein phosphorylation of Akt3 indicates Akt3 activity. Akt3 phosphorylation may be determined at Serine 472, as described herein. Alternatively or additionally, phosphorylation may be determined at threonine 305 and/or tyrosine 174.

In some embodiments, Akt3 activity is assessed by determining the intracellular localisation of Akt3 protein, wherein localisation in the nucleus indicates active Akt3.

In some embodiments, Akt3 activity is assessed by determining the expression levels of downstream targets, for example genes associated with EMT. In further embodiments, Akt3 kinase activity may be assessed by determining phosphorylation of substrate proteins (e.g. SNAIL) or peptides, for example as described in Tuomi et al., 2009.

Akt3

Akt3 (also known as PKB gamma) is present in two isoforms in humans, isoform 1 and isoform 2. The sequence of isoform 1 (Q9Y23, version 1), which is the "canonical" sequence is as follows:

SEQ ID NO: 1
MSDVTIVKEGWVQKRGEYIKNWRPRYFLLKTDGSFIGYKEKPQDVDLPY

PLNNFSVAKCQLMKTERPKPNTFIIRCLQWTTVIERTFHVDTPEEREEW

TEAIQAVADRLQRQEEERMNCSPTSQIDNIGEEEMDASTTHHKRKTMND

FDYLKLLGKGTFGKVILVREKASGKYYAMKILKKEVIIAKDEVAHTLTE

SRVLKNTRHPFLTSLKYSFQTKDRLCFVMEYVNGGELFFHLSRERVFSE

DRTRFYGAEIVSALDYLHSGKVIYRDLKLENLMLDKDGHIKITDFGLCK

EGITDAATMKTFCGTPEYLAPEVLEDNDYGRAVDWWGLGVVMYEMMCGR

LPFYNQDHEKLFELILMEDIFKPRTLSSDAKSLLSGLLIKDPNKRLGGG

PDDAKEIMRHSFFSGVNWQDVYDKKLVPPFKPQVTSETDTRYFDEEFTA

QTITITPPEKYDEDGMDCMDNERRPHFPQFSYSASGRE

Isoform 2 has the sequence:

SEQ ID NO: 2
MSDVTIVKEGWVQKRGEYIKNWRPRYFLLKTDGSFIGYKEKPQDVDLPY

PLNNFSVAKCQLMKTERPKPNTFIIRCLQWTTVIERTFHVDTPEEREEW

TEAIQAVADRLQRQEEEMNCSPTSQIDNIGEEEMDASTTHHKRKTMNDF

DYLKLLGKGTFGKVILVREKASGKYYAMKILKKEVIIAKDEVAHTLTES

RVLKNTRHPFLTSLKYSFQTKDRLCFVMEYVNGGELFFHLSRERVFSED

RTRFYGAEIVSALDYLHSGKIVYRDLKLENLMLDKDGHIKITDFGLCKE

GITAATMKTFCGTPEYLAPEVLEDNDYGRAVDWWGLGVVMYEMMCGRLP

FYNQDHEKLFELILMEDIKFPRTLSSDAKSLLSGLLIKDPNKRLGGGPD

DAKEIMRHSFFSGVNWQDVYDKKLVPPFKPQVTSETDTRYFDEEFTAQT

ITITPPEKCQQSDCGMLGNWKK

Measuring Altered Expression of Gene/Protein Markers

Levels of gene and protein expression may be determined using a number of different techniques, (a) At the RNA Level Gene expression can be detected at the RNA level. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilising ribonucleic acid hybridisation include nuclear run-on assays, RT-PCR, RNase protection assays (Melton et al., Nuc. Acids Res. 12:7035), Northern blotting and In Situ hybridization. Gene expression can also be detected by microarray analysis as described below.

For Northern blotting, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

Nuclease Protection Assays (including both ribonuclease protection assays and S1 nuclease assays) provide an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. NPAs allow the simultaneous detection of several RNA species.

In situ hybridization (ISH) is a powerful and versatile tool for the localization of specific mRNAs in cells or tissues. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. Alternatively, tissue can be sectioned frozen and post-fixed in paraformaldehyde. After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents. This latter method of detection is the basis for Fluorescent In Situ Hybridisation (FISH).

Methods for detection which can be employed include radioactive labels, enzyme labels, chemiluminescent labels, fluorescent labels and other suitable labels.

Typically, RT-PCR is used to amplify RNA targets. In this process, the reverse transcriptase enzyme is used to convert RNA to complementary DNA (cDNA) which can then be amplified to facilitate detection. Relative quantitative RT-PCR involves amplifying an internal control simultaneously with the gene of interest. The internal control is used to normalize the samples. Once normalized, direct comparisons of relative abundance of a specific mRNA can be made across the samples. Commonly used internal controls include, for example, GAPDH, HPRT, actin and cyclophilin.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification (TAS) methods have been described in the literature, for example, general reviews of these methods in Landegren, U. et al., Science 242:229-237 (1988) and Lewis, R., Genetic Engineering News 10:1, 54-55 (1990).

PCR is a nucleic acid amplification method described inter alia in U.S. Pat. Nos. 4,683,195 and 4,683,202. PCR can be used to amplify any known nucleic acid in a diagnostic context (Mok et al., 1994, Gynaecologic Oncology 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, Proc. Natl. Acad. Sci. USA 87:1874). Ligation amplification reaction or ligation amplification system uses DNA ligase and four oligonucleotides, two per target strand. This technique is described by Wu, D. Y. and Wallace, R. B., 1989, Genomics 4:560. In the Qβ Replicase technique, RNA replicase for the bacteriophage Qβ, which replicates single-stranded RNA, is used to amplify the target DNA, as described by Lizardi et al., 1988, Bio/Technology 6:1197.

Quantitative PCR (Q-PCR) is a technique which allows relative amounts of transcripts within a sample to be determined. A suitable method for performing QPCR is described herein.

Alternative amplification technology can be exploited in the present invention. For example, rolling circle amplification (Lizardi et al., 1998, *Nat Genet* 19:225) is an amplification technology available commercially (RCAT™) which is driven by DNA polymerase and can replicate circular oligonucleotide probes with either linear or geometric kinetics under isothermal conditions. A further technique, strand displacement amplification (SDA; Walker et al., 1992, *Proc. Natl. Acad. Sci. USA* 80:392) begins with a specifically defined sequence unique to a specific target.

Suitable probes for detecting the expression of Akt3 or Akt2 identified herein may conveniently be packaged in the form of a test kit in a suitable container. In such kits the probe may be bound to a solid support where the assay format for which the kit is designed requires such binding. The kit may also contain suitable reagents for treating the sample to be probed, hybridising the probe to nucleic acid in the sample, control reagents, instructions, and the like. Suitable kits may comprise, for example, primers for a QPCR reaction or labelled probes for performing FISH.

(b) At the Polypeptide Level

Altered gene or protein expression may also be detected by measuring the polypeptides encoded by the Akt3 or Akt2 gene. This may be achieved by using molecules which bind to the polypeptides encoded by Akt3 or Akt2 gene. Suitable molecules/agents which bind either directly or indirectly to the polypeptides in order to detect the presence of the protein include naturally occurring molecules such as peptides and proteins, for example antibodies, or they may be synthetic molecules.

Antibodies for the Akt3 or Akt2 genes or proteins may be derived from commercial sources or through techniques which are familiar to those skilled in the art. In one embodiment, and where altered expression manifests itself through the expression of alteration of post translationally-modified forms of as protein biomarker, antibodies specific for those different forms may be used.

Methods for production of antibodies are known by those skilled in the art. If polyclonal antibodies are desired, a selected mammal (e.g., mouse, rabbit, goat, horse, etc.) is immunised with an immunogenic polypeptide bearing an epitope(s) from a polypeptide. Serum from the immunised animal is collected and treated according to known procedures. If serum containing polyclonal antibodies to an epitope from a polypeptide contains antibodies to other antigens, the polyclonal antibodies can be purified by immunoaffinity chromatography. Techniques for producing and processing polyclonal antisera are known in the art. In order to generate a larger immunogenic response, polypeptides or fragments thereof may be haptenised to another polypeptide for use as immunogens in animals or humans.

Monoclonal antibodies directed against epitopes in polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes in the polypeptides of the invention can be screened for various properties; i.e., for isotype and epitope affinity. An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes whole antibodies, or fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP239400A. For example: monoclonal and polyclonal antibodies, recombinant antibodies, proteolytic and recombinant fragments of antibodies (Fab, Fv, scFv, diabodies), single-domain antibodies (VHH, sdAb, nanobodies, IgNAR, VNAR), and proteins unrelated to antibodies, which have been engineered to have antibody-like specific binding, such as the following:

Name Based on:
Affibodies Protein A, Z domain 6 kDa
Affitins Sac7d (from *Sulfolobus acidocaldarius*) 7 kDa
Anticalins Lipocalins 20 kDa
DARPins Ankyrin repeat motif 14 kDa
Fynomers Fyn, SH3 domain 7 kDa
Kunitz domain peptides Various protease inhibitors 6 kDa
Monobodies Fibronectin Standard laboratory techniques such as immunoblotting as described above can be used to detect altered levels of Akt3 or Akt2 activity, as compared with untreated cells in the same cell population.

Gene expression may also be determined by detecting changes in post-translational processing of polypeptides or post-transcriptional modification of nucleic acids. For example, differential phosphorylation of polypeptides, the cleavage of polypeptides or alternative splicing of RNA, and the like may be measured. Levels of expression of gene products such as polypeptides, as well as their post-translational modification, may be detected using proprietary protein assays or techniques such as 2D polyacrylamide gel electrophoresis.

Antibodies may be used for detecting Akt3 or Akt2 expression by a method which comprises: (a) providing an antibody; (b) incubating a biological sample with said antibody under conditions which allow for the formation of an antibody-antigen complex; and (c) determining whether antibody-antigen complex comprising said antibody is formed.

Suitable samples include extracts of tissues such as brain, breast, ovary, lung, colon, pancreas, testes, liver, muscle and bone tissues or from neoplastic growths derived from such tissues. Other suitable examples include blood or urine samples.

Antibodies that specifically bind to Akt3 or Akt2 proteins can be used in diagnostic or prognostic methods and kits that are well known to those of ordinary skill in the art to detect or quantify the expression of Akt3 or Akt2 protein in a body fluid or tissue. Results from these tests can be used to diagnose or predict the occurrence or recurrence of cancer and other cell motility or cell survival-mediated diseases, or to assess the effectiveness of drug dosage and treatment.

Antibodies can be assayed for immunospecific binding by any method known in the art. The immunoassays which can be used include but are not limited to competitive and non-competitive assay systems using techniques such as western blots, immunohistochemistry, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such assays are routine in the art (see, for example, Ausubel et al., eds, 1994, *Current Protocols in Molecular Biology*, Vol. 1, John Wiley & Sons, Inc., New York, which is incorporated by reference herein in its entirety).

Antibodies for use in the invention are preferably bound to a solid support and/or packaged into kits in a suitable container along with suitable reagents, controls, instructions and the like.

Other methods include, but are not limited to, 2D-PAGE although this is less suitable for large-scale screening. Newer techniques include matrix-assisted laser desorption ionization time of flight mass spectrometry (MALDI-TOF MS). In MALDI-TOF analysis, proteins in a complex mixture are affixed to a solid metallic matrix, desorbed with a pulsed laser beam to generate gas-phase ions that traverse a field-free flight tube, and are then separated according to their mass-dependent velocities. Individual proteins and peptides can be identified through the use of informatics tools to search protein and peptide sequence databases. Surface-enhanced laser desorption/ionisation time of flight MS (SELDI-TOF MS) is an affinity-based MS method in which proteins are selectively adsorbed to a chemically modified solid surface, impurities are removed by washing, an energy-absorbing matrix is applied, and the proteins are identified by laser desorption mass analysis.

SELDI-TOF-MS can be used for the detection of the appearance/loss of either intact proteins or fragments of specific proteins. In addition SELDI-TOF-MS can also be used for detection of post translational modifications of proteins due to the difference in mass caused by the addition/removal of chemical groups. Thus phosphorylation of a single residue will cause a mass shift of 80 Da due to the phosphate group. A data base of molecular weights that can be attributed to post-translational modifications is freely accessible on the internet (http://www.abrf.org/index/cfm/dm.home?avgmass=all). Moreover specific polypeptides can be captured by affinity-based approaches using SELDI-TOF-MS by employing antibodies that specifically recognise a post-translationally modified form of the protein, or that can recognise all forms of the protein equally well.

Arrays

Array technology and the various techniques and applications associated with it is described generally in numerous textbooks and documents. These include Lemieux et al., 1998, *Molecular Breeding* 4:277-289; Schena and Davis. *Parallel Analysis with Biological Chips, in PCR Methods Manual* (eds. M. Innis, D. Gelfand, J. Sninsky); Schena and Davis, 1999, *Genes, Genomes and Chips. In DNA Microarrays: A Practical Approach* (ed. M. Schena), Oxford University Press, Oxford, UK, 1999); *The Chipping Forecast* (*Nature Genetics* special issue; January 1999 Supplement); Mark Schena (Ed.), *Microarray Biochip Technology*, (Eaton Publishing Company); Cortes, 2000, *The Scientist* 14(17): 25; Gwynne and Page, *Microarray analysis: the next revolution in molecular biology, Science*, 1999, August 6; Eakins and Chu, 1999, *Trends in Biotechnology*, 17:217-218, and also at various world wide web sites.

Array technology overcomes the disadvantages with traditional methods in molecular biology, which generally work on a "one gene in one experiment" basis, resulting in low throughput and the inability to appreciate the "whole picture" of gene function. Currently, the major applications for array technology include the identification of sequence (gene/gene mutation) and the determination of expression level (abundance) of genes. Gene expression profiling may make use of array technology, optionally in combination with proteomics techniques (Celis et al., 2000, *FEBS Lett*, 480(1):2-16; Lockhart and Winzeler, 2000, *Nature* 405 (6788):827-836; Khan et al., 1999, 20(2):223-9). Other applications of array technology are also known in the art; for example, gene discovery, cancer research (Marx, 2000, *Science* 289: 1670-1672; Scherf et al et al, 2000, *Nat Genet* 24(3):236-44; Ross et N., 2000, *Nat Genet* 2000, 24(3):227-35), SNP analysis (Wang et al., 1998, *Science* 280(5366): 1077-82), drug discovery, pharmacogenomics, disease diagnosis (for example, utilising microfluidics devices: *Chemical & Engineering News*, Feb. 22, 1999, 77(8):27-36), toxicology (Rockett and Dix (2000), *Xenobiotica* 30(2):155-77; Afshari et al. 1999, *Cancer Res* 59(19):4759-60) and toxicogenomics (a hybrid of functional genomics and molecular toxicology). The goal of toxicogenomics is to find correlations between toxic responses to toxicants and changes in the genetic profiles of the objects exposed to such toxicants (Nuwaysir et al., 1999, *Molecular Carcinogenesis* 24:153-159).

In the context of the present invention, inlay technology can be used, for example, in the analysis of the expression of Akt3 or Akt2 protein or mRNA. In one embodiment, array technology may be used to assay the effect of a candidate compound on Akt3 activity.

In general, any library or group of samples may be arranged in an orderly manner into an array, by spatially separating the members of the library or group. Examples of suitable libraries for arraying include nucleic acid libraries (including DNA, cDNA, oligonucleotide, etc. libraries), peptide, polypeptide and protein libraries, as well as libraries comprising any molecules, such as ligand libraries, among others. Accordingly, where reference is made to a "library" in this document, unless the context dictates otherwise, such reference should be taken to include reference to a library in the form of an array.

The samples (e.g., members of a library) are generally fixed or immobilised onto a solid phase, preferably a solid substrate, to limit diffusion and admixing of the samples. In a preferred embodiment, libraries of DNA binding ligands may be prepared. In particular, the libraries may be immobilised to a substantially planar solid phase, including membranes and nonporous substrates such as plastic and glass. Furthermore, the samples are preferably arranged in such a way that indexing (i.e., reference or access to a particular sample) is facilitated. Typically the samples are applied as spots in a grid formation. Common assay systems may be adapted for this purpose. For example, an array may be immobilised on the surface of a microplate, either with multiple samples in a well, or with a single sample in each well. Furthermore, the solid substrate may be a membrane, such as a nitrocellulose or nylon membrane (for example, membranes used in blotting experiments). Alternative substrates include glass, or silica based substrates. Thus, the samples are immobilised by any suitable method known in the art, for example, by charge interactions, or by chemical coupling to the walls or bottom of the wells, or the surface of the membrane.

Other means of arranging and fixing may be used, for example, pipetting, drop-touch, piezoelectric means, ink-jet and bubblejet technology, electrostatic application, etc. In the case of silicon-based chips, photolithography may be utilised to arrange and fix the samples on the chip.

The samples may be arranged by being "spotted" onto the solid substrate; this may be done by hand or by making use of robotics to deposit the sample. In general, arrays may be described as macroarrays or microarrays, the difference being the size of the sample spots. Macroarrays typically contain sample spot sizes of about 300 microns or larger and may be easily imaged by existing gel and blot scanners. The sample spot sizes in microarrays are typically less than 200 microns in diameter and these arrays usually contain thousands of spots. Thus, microarrays may require specialized robotics and imaging equipment, which may need to be custom made. Instrumentation is described generally in a review by Cortese, 2000, *The Scientist* 14(11):26.

Techniques for producing immobilised libraries of DNA molecules have been described in the art. Generally, most prior art methods described how to synthesise single-stranded nucleic acid molecule libraries, using for example masking techniques to build up various permutations of sequences at the various discrete positions on the solid substrate. U.S. Pat. No. 5,837,832, the contents of which are incorporated herein by reference, describes an improved method for producing DNA arrays immobilised to silicon substrates based on very large scale integration technology. In particular, U.S. Pat. No. 5,837,832 describes a strategy called "tiling" to synthesize specific sets of probes at spatially-defined locations on a substrate which may be used to produced the immobilised DNA libraries of the present invention. U.S. Pat. No. 5,837,832 also provides references for earlier techniques that may also be used.

Arrays of peptides (or peptidomimetics) may also be synthesised on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a target or probe) and reactive library members occur is determined, thereby identifying the sequences of the reactive library members on the basis of spatial location. These methods are described in U.S. Pat. No. 5,143,854; WO 90/15070 and WO 92/10092; Fodor et al., 1991, *Science* 251:767; Dower and Fodor, 1991, *Ann. Rep. Med. Chem.* 26:271.

To aid detection, targets and probes may be labelled with any readily detectable reporter, for example, a fluorescent, bioluminescent, phosphorescent, radioactive, etc reporter. Such reporters, their detection, coupling to targets/probes, etc are discussed elsewhere in this document. Labelling of probes and targets is also disclosed in Shalon et al, 1996, *Genome Res* 6(7):639-45.

Specific examples of DNA arrays include the following:

Format I: probe cDNA (~500-~5,000 bases long) is immobilized to a solid surface such as glass using robot spotting and exposed to a set of targets either separately or in a mixture. This method is widely considered as having been developed at Stanford University (Ekins and Chu, 1999, *Trends in Biotechnology,* 17:217-218).

Format II: an array of oligonucleotide (~20-~25-mer oligos) or peptide nucleic acid (PNA) probes is synthesized either in situ (on-chip) or by conventional synthesis followed by on-chip immobilization. The array is exposed to labeled sample DNA, hybridized, and the identity/abundance of complementary sequences are determined. Such a DNA chip is sold by Affymetrix, Inc., under the GeneChip® trademark.

Examples of some commercially available microarray formats are set out, for example, in Marshall and Hodgson, 1998, *Nature Biotechnology* 16(1):27-31.

Data analysis is also an important part of an experiment involving arrays. The raw data from a microarray experiment typically are images, which need to be transformed into gene expression matrices—tables where rows represent for example genes, columns represent for example various samples such as tissues or experimental conditions, and numbers in each cell for example characterize the expression level of the particular gene in the particular sample. These matrices have to be analyzed further, if any knowledge about the underlying biological processes is to be extracted. Methods of data analysis (including supervised and unsupervised data analysis as well as bioinformatics approaches) are disclosed in Brazma and Vilo J, 2000, *FEBS Lett* 480(1): 17-24.

As disclosed above, proteins, polypeptides, etc may also be immobilised in arrays. For example, antibodies have been used in microarray analysis of the proteome using protein chips (Borrcbaeck C A, 2000, *Immunol Today* 21(8):379-82). Polypeptide arrays are reviewed in, for example, MacBeath and Schreiber, 2000, *Science,* 289(5485):1760-1763.

Pharmaceutical Composition

A further aspect relates to a pharmaceutical composition comprising an Akt3 inhibitor or other agent identified according to any of the above-described methods admixed with a pharmaceutically acceptable diluent, excipient or carrier.

For use according to the present invention, the agent may be presented as a pharmaceutical formulation, comprising the compounds or physiologically acceptable salt, ester or other physiologically functional derivative thereof, together with one or more pharmaceutically acceptable carriers and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients", 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition.

Examples of preservatives include sodium benzoate, sorbic acid and esters of p hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active agent. A tablet may be made by compression or moulding, optionally with one or more accessory ingredients. Compressed tablets may be prepared by compressing in a suitable machine an active agent in a free-flowing form such as a powder or granules optionally mixed with a binder, lubricant, inert diluent, lubricating agent, surface-active agent or dispersing agent. Moulded tablets may be made by moulding an active agent with an inert liquid diluent. Tablets may be optionally coated and, if uncoated, may optionally be scored. Capsules may be prepared by filling an active agent, either alone or in admixture with one or more accessory ingredients, into the capsule shells and then sealing them in the usual manner. Cachets are analogous to capsules wherein an active agent together with any accessory ingredient(s) is sealed in a rice paper envelope. An active agent may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active agent is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active agent with the softened or melted carrier(s) followed by chilling and shaping in moulds.

Pharmaceutical formulations suitable for parenteral administration include sterile solutions or suspensions of an active agent in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active agent may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active agent, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active agent is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active agent may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active agent in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing an agent into association with a pharmaceutically or veterinarily acceptable carrier or vehicle.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid, emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellutose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier. Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of agent may be administered to inhibit Akt3. Of course, this dosage amount will further be modified according to the type of administration of the agent. For example, to achieve an "effective amount" for acute therapy, parenteral administration is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase. The agents may be administered one to four times daily at a level to achieve a total daily dose of about 0.4 to about 400 mg/kg/day. The precise amount of an active agent which is therapeutically effective, and the route by which such agent is best administered, is readily determined by one of ordinary skill in the art by comparing the blood level of the agent to the concentration required to have a therapeutic effect.

The agents of this invention may also be administered orally to the patient, in a manner such that the concentration of drug is sufficient to achieve one or more of the therapeutic indications disclosed herein. Typically, a pharmaceutical composition containing the agent is administered at an oral dose of between about 0.1 to about 50 mg/kg in a manner consistent with the condition of the patient. Preferably the oral dose would be about 0.5 to about 20 mg/kg.

The agents of this invention may be tested in one of several biological assays to determine the concentration of an agent which is required to have a given pharmacological effect.

Kit of Parts

Another aspect of the invention relates to a kit comprising an Akt3 inhibitor, anti-Akt3 antibody, nucleic acid probe for Akt3 or at least one QPCR primer for Akt3, for use in any of the above-described methods.

Diagnostics and Prognostics

The invention also relates to the use of Akt3 as a biomarker in the diagnosis or prognosis of diseases characterized by proliferative activity, particularly in individuals being treated with Akt3 inhibitors.

As used herein, the term "prognostic method" means a method that enables a prediction regarding the progression of a disease of a human or animal diagnosed with the disease, in particular, cancer. More specifically, the cancers of interest include breast, lung, gastric, head and neck, colorectal, renal, pancreatic, uterine, hepatic, bladder, endometrial and prostate cancers and leukemias.

The term "diagnostic method" as used herein means a method that enables a determination of the presence or type of cancer in or on a human or animal. Suitably the marker allows the success of treatment with an Akt3 inhibitor to be assessed. As discussed above, suitable diagnostics include probes directed to any of the genes as identified herein such as, for example, QPCR primers, FISH probes and so forth.

The term "prognostic method" as used herein means a method that enables a determination of the likelihood of a subject being susceptible or responsive to treatment with a particular agent/regimen. Such prognostic methods provide information on the likely outcome of a particular treatment regimen, for example, the likelihood of a subject responding to said treatment, and/or information as to how aggressively an individual should be treated within a particular treatment regimen, and/or how aggressively an individual should be treated with conventional therapeutic methods such as radiation/chemotherapy. The prognostic methods described herein therefore have important applications in the field of personalised medicines.

One preferred embodiment thus relates to the use of a biomarker as described above in a personalised medicine application.

In one preferred embodiment, the personalised medicine application is for determining whether a subject will be susceptible or responsive to treatment with an Akt3 or Axl inhibitor.

In one preferred embodiment, the personalised medicine application is for determining whether a subject is particularly likely to suffer from metastatic cancer.

Another aspect of the invention relates to a prognostic method for determining whether a subject will be susceptible to treatment with an Akt3 or Axl inhibitor, said method comprising detecting the occurrence of epithelial-to-mesenchymal transition (EMT) in said subject.

Another aspect of the invention relates to the use of Akt3 as a biomarker in a prognostic agent for determining whether a subject will be susceptible or responsive to treatment with an Akt3 or Axl inhibitor.

Another aspect of the invention relates to a prognostic method for determining whether a subject is particularly likely to suffer from metastatic cancer, said method comprising detecting the occurrence of epithelial-to-mesenchymal transition (EMT) in said subject.

Throughout the specification, preferably the methods described herein are performed in vitro or ex vivo.

The invention will now be described in more detail, by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

BRIEF DESCRIPTION OF THE DRAWINGS

FIG. 13 shows cells expressing constitutively active Akt3 show a much higher ability to form tumors than cells expressing constitutively active Akt1

EXAMPLES

Example 1 When Breast Epithelial Cells Undergo EMT, Akt3 is Up-Regulated while Akt2 is Down-Regulated, and these Changes are Axl-Dependent MCF10A cells (American Type Culture Collection), a breast epithelial cell line used as a model for normal breast epithelial cells were cultured in DMEM/F12 medium supplemented with 5% horse serum, 20 ng/ml, EGF, 0.5 µg/mL, hydrocortisone, 100 ng/mL cholera toxin, 10 µg/mL insulin, 100 U/mL penicillin and 100 µg/mL streptomycin (Sigma-Aldrich). MCF10A cells were used in this experiment along with a retroviral vector ("Slug") driving expression of the EMT inducer Slug and a retroviral vector ("Axl2") driving expression of a shRNA that knocks down expression of Axl (vectors described in (Gjerdrum C et al. Axl is an essential epithelial-to-mesenchymal transition-induced regulator of breast cancer metastasis and patient survival. Proc Natl Acad Sci USA. 2010 Jan. 19; 107(3): 1124-9). Briefly, Axl shRNA was expressed from a modified human U6 promoter in the LTR of the retroviral vectors RRI-Red/L087 (GenBank; EU424173), while the human Slug cDNA sequence from BC012910 (Open Biosystems) was cloned into the CRU5-IRES-CFP retroviral vector (Lorens J B, Jang Y, Rossi A B, Payan D C, Bogenberger J M (2000) Optimization of regulated LTR-mediated expression. Virology 272:7-15). MCF10A cells were transduced with either retroviral vector "Slug" alone or with a combination of both the "Slug" and "Axl2" retroviral vectors. Control cells were transduced with neither vector. Protein extracts were prepared from the control and transduced cell populations by lysis in RIPA buffer (PBS with 1% (vol/vol) Nonidet P-40 (Nonidet P-40), 0.5% (wt/vol) sodium deoxycholate, and 0.1% (wt/vol) SDS) supplemented with protease inhibitor (13457200; Roche) and 0.2 mM PMSF. Protein concentration was determined by Bradford assay (BioRad), and 50 µg of total protein was loaded in each well of SDS/PAGE. Running of gel and immunoblotting were carried out according to standard procedures. The antibodies used were mouse monoclonal anti-human Axl (MAB154; R&D Systems), AKT1 (Cell Signaling #2967), Akt2 (Cell Signaling #3063), Akt3 (Millipore #1586912), pAKT (Ser473, Cell Signaling 2971), α-actin (Sigma-Aldrich), pERK (Cell Signaling #4695). The pAKT antibody reacts with Akt1, Akt2 and Akt3 when they are phosphorylated at the amino-acid corresponding to Ser473 in Akt1.

Figure 1:
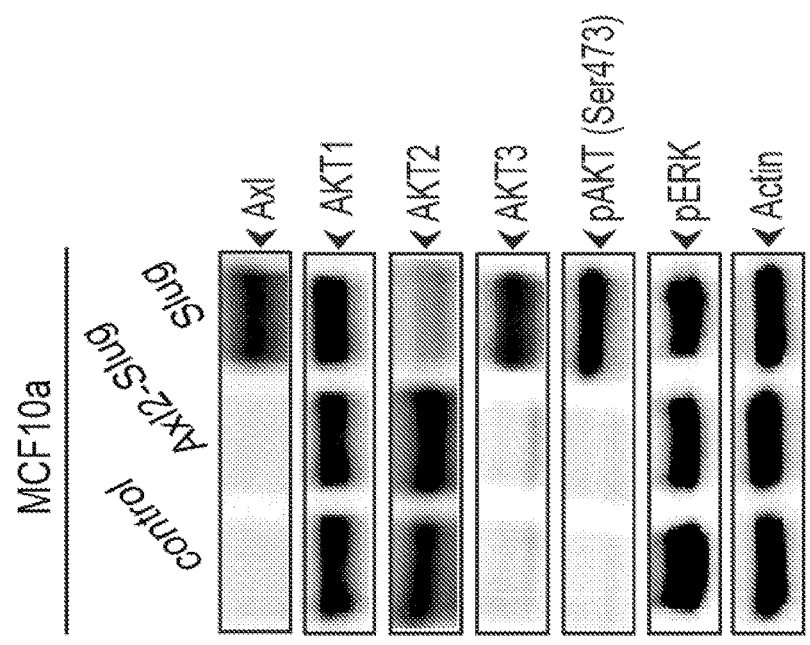
FIG. 1 is a set of photographs of immunoblots depicting results of experiments on breast epithelial cells undergoing EMT.

The results of these experiments are shown in FIG. 1. As expected, pAKT is increased in the cells undergoing EMT (compare Control, Slug lanes), and this increase is blocked when EMT is blocked by knocking down Axl (compare Control, Slug, Axl2-Slug lanes). Unexpectedly, Akt3 expression is strongly upregulated when these breast epithelial cells undergo EMT. In contrast, Akt1 expression remains constant and Akt2 is down-regulated. Blocking Axl in EMT induced cells (Axl2-Slug lane) also blocks the switch in Akt isoform indicating that the change in expression from Akt2 to Akt3 depends on Axl. Note that activated (phosphorylated) Akt (pAkt) follows Akt3 levels, and not Akt1 and 2 levels, suggesting that the major phospho-Akt isoform in these cells may be Akt3. This is confirmed in Example 4.

Example 2 When Transformed Breast Cancer Cells Undergo EMT, Akt3 is Up-Regulated, and these Changes are Axl-Dependent HMLE and HMLER cells (Elenbaas B, Spiric L, and Weinberg R A. Human breast cancer cells generated by oncogenic transformation of primary mammary epithelial cells. Genes Dev. 2001 Jan. 1; 15(1):50-65),), experimentally transformed breast cancer cell lines, were cultured in MEGM (Lonza)/DMEMF12 (Sigma-Aldrich) medium supplemented with 5 ng/mL EGF, 10 µg/mL insulin, 0.5 µg/mL hydrocortisone, 100 U/mL penicillin and 100 µg/mL streptomycin (Sigma-Aldrich). Cells were transduced with either retroviral vectors "Slug", "Axl2", control luciferase shRNA (ctr), or with a combination of both the "Slug" and "Axl2" retroviral vectors as described in Example 1. Preparation of protein extracts, running of gel, immunoblotting and probing of membranes were performed as described in Example 1.

Figure 2:
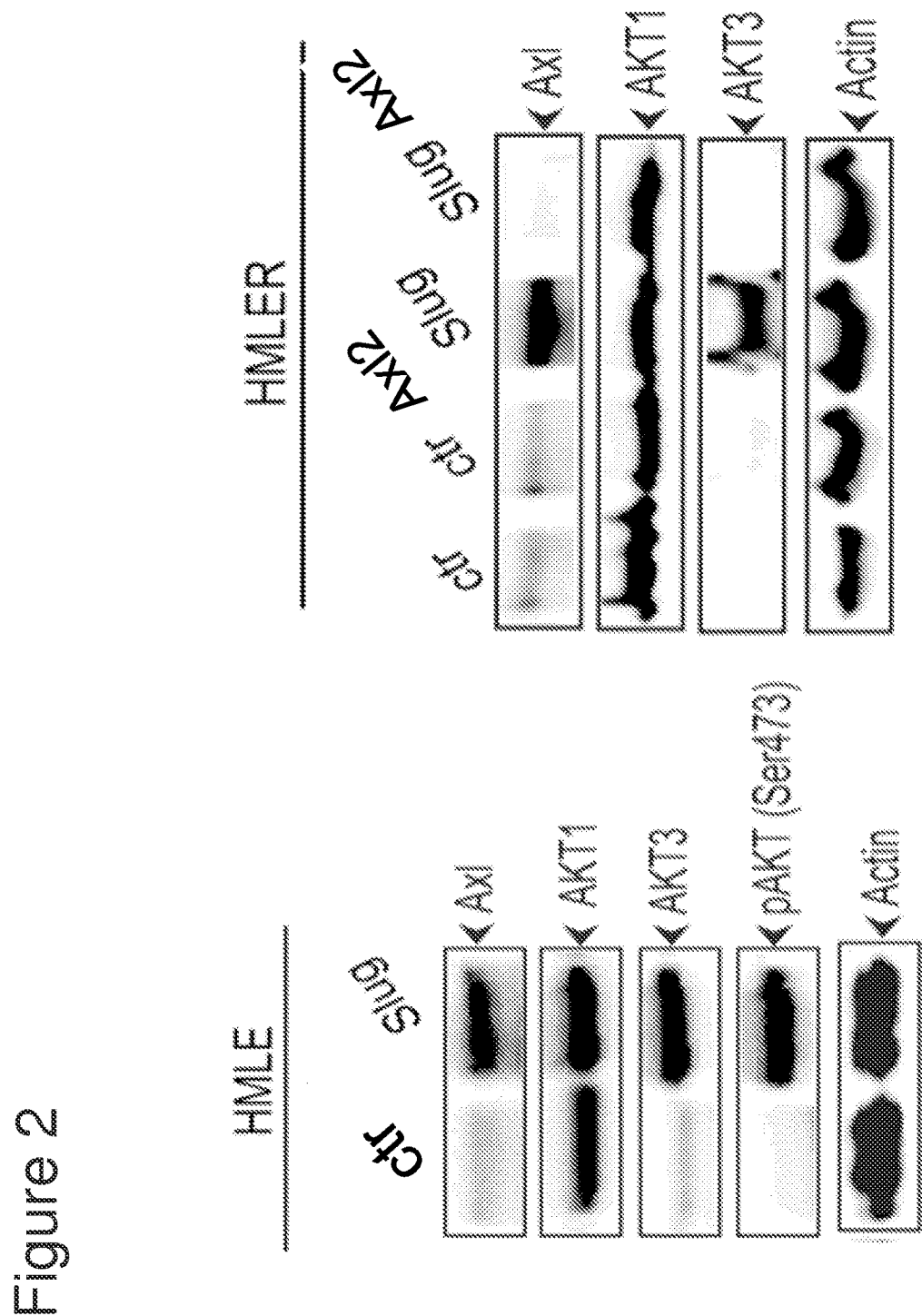
FIG. 2 shows Akt3 is up-regulated when breast cancer cells undergo EMT, and these changes are Axl-dependent.

The results of these experiments are shown in FIG. 2. As found in Example 1, Akt3 expression is strongly upregulated when these breast epithelial cells undergo EMT (compare Control, Slug lanes), HMLE cells (left): Activated (phosphorylated) Akt (pAkt) follows Akt3 levels, and not Akt1 levels (compare Control and Slug lanes). HMLER cells (right): Blocking Axl in EMT induced cells (Slug-Axl2 lane) also blocks Akt3 expression, indicating that Akt3 expression levels depends on Axl.

Example 3 Akt3, and not Akt1 is Downregulated in Response to Axl Inhibition in Triple Negative Breast Cancer Cells MDA-MB231 cells (American Type Culture Collection), a triple negative breast cancer cell line, were cultured in F12 media supplemented with 10% fetal bovine serum, 100 U/mL penicillin and 100 µg/mL streptomycin (Sigma-Aldrich). The cells were transduced with retroviral constructs expressing shAxl ("Axl2") or control luciferase shRNA ("control") as described in Example 1 and Example 2. Preparation of protein extracts, running of gel, immunoblotting and probing of membranes were performed as described in Example 1 and 2.

Figure 3:
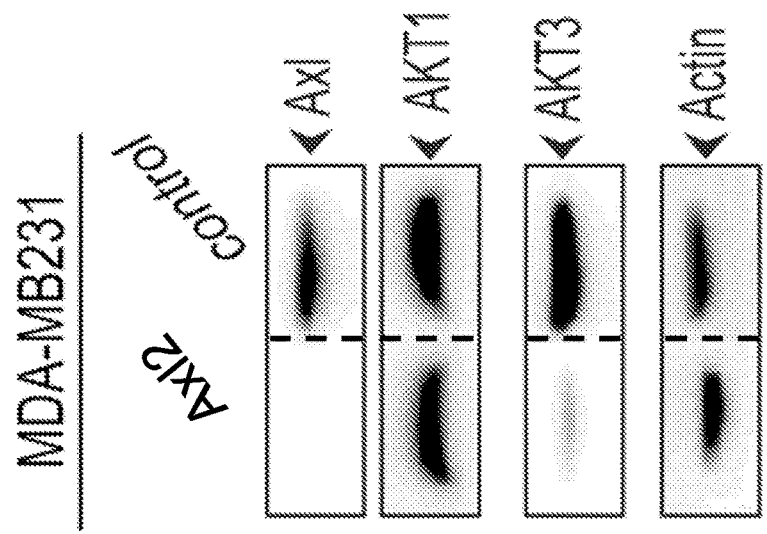
FIG. 3 shows Akt3, and not Akt1 is downregulated in response to Axl inhibition in triple negative breast cancer cells.

Results are shown in FIG. 3. MDA-MB231 cells express Axl, Akt1 and Akt3 (see "control" lane). In line with data shown in Example 1 and 2, blocking of Axl ("Axl2"), also blocks Akt3 expression, but has no significant effect on Akt1 expression, indicating that Akt3, but not Akt1, expression levels depends on Axl.

Example 4 Akt3 Represents the Major P-Akt Isoform in MCF10A Cells Induced to Undergo EMT (by TGF β Treatment)

MCF10A cells were treated with TGF β (10 ng/ml) for 4 days. Cells were then lysed using NP40 Cell Lysis Buffer (40 mM HepesNAOH, 75 mM NaCl, 2 mM EDTA, 1% NP40, phosphatase inhibitor cocktail tablet, protease inhibitor cocktail tablet (Roche)), scraped off the plate, rotated at 4° C. for 30 min, centrifuged at 13000 rpm for 10 min, and supernatant harvested. For immunoprecipitation, Akt1 (2H10, Cell Signaling #2967), Akt2 (Cell Signaling #3063), Akt3 (Millipore #07-383) and control IgG (Abeam) antibodies (1 μg/lysate) were added to lysates and incubated overnight at 4° C. Next day the pre-blocked protein-G beads (GE Healthcare) in lysis buffer were added and allowed to bind at 4° C. for 1 hour. Beads were then washed 3 times (20 mM Tris-HCl (pH 7.5), 150 mM NaCl, 1% NP40), protein eluted by boiling in SDS-PAGE loading buffer. Running of SDS/PAGE and immunoblotting were carried out according to standard procedures. Membrane was probed using pAktS473 (Cell Signaling #9271) and PAN-Akt (Cell Signaling #9272) antibodies.

Figure 4:
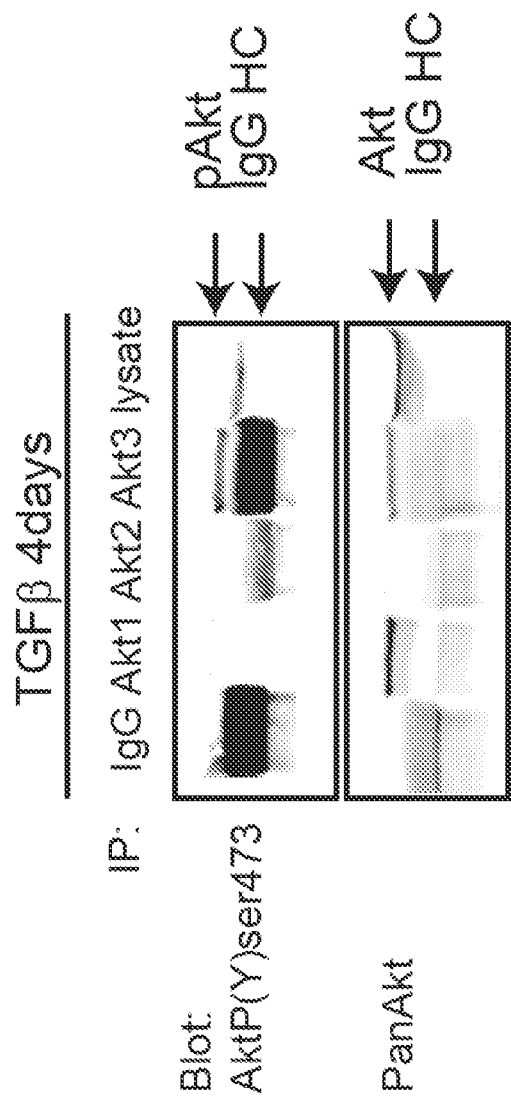
FIG. 4 is a set of photographs of immunoblots determining levels of isoforms in EMT-induced breast cancer cells.

These data, shown in FIG. 4, demonstrate that phospho-Akt3 represents the major pAkt isoform in EMT-induced MCF10A cells. No phospho-Akt1 was detected. This was unexpected in view of the previous studies suggesting that Akt1 was responsible for the effects of Akt.

Example 5 Akt3, but not Akt 1 and 2 mRNA Correlate with EMT and Stem Genes in Breast Cancer Cells and Breast Cancer Biopsies The expression analysis of the breast cancer cell lines and human breast cancer biopsy samples (cancer, normal) was performed from published and GEO-submitted Affymetrix data as described (Kilpinen S, Autio R, Ojala K, Iljin K, Bucher E, Sara H, Pisto T, Saarela M, Skotheim R I, Björkman M, Mpindi J P, Haapa-Paananen S, Vainio P, Edgren H, Wolf M, Astola J, Nees M, Hautaniemi S. Kallioniemi O. Systematic bioinformatic analysis of expression levels of 17,330 human genes across 9,783 samples from 175 types of healthy and pathological tissues. Genome Biol. 2008; 9(9):R139.) Positive correlation is indicated with a plus (+) sign, darker gray indicate stronger positive correlation, and higher confidence is indicated with increasing number of asterisks (*). Similarly, negative correlation is indicated with a minus (−) sign, darker gray indicate stronger negative correlation, and higher confidence is indicated with increasing number of asterisks (*).

| Gene | Epithelial marker | Mesenchymal marker | EMT-mediator | Cancer Stem Cell marker |
|---|---|---|---|---|
| SOX2 | | | X | X |
| SNAI1 | | | X | |
| CD44 | | | X | X |
| SEMA3C | | X? | | |
| TWIST1 | | | X | |
| ZEB1 | | | X | |
| CDH2 | | X | | |
| ID4 | | | | X |
| VIM | | X | | |
| ZEB1 | | | X | |
| AXL | | | X | X |
| SNAI2 | | | X | |
| PLXNA2 | | | | X |

Figure 5:
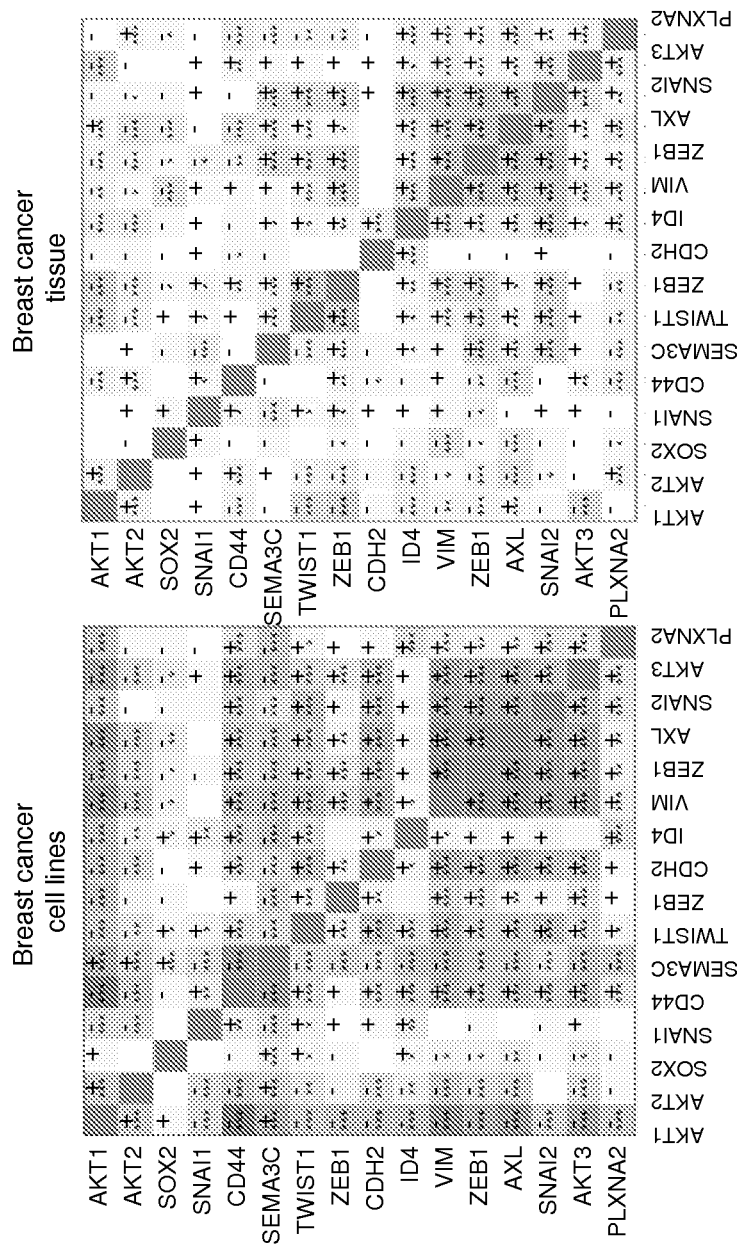
FIG. 5 shows Akt3, but not Akt 1 and 2 mRNA correlate with EMT and stem genes in breast cancer cells and breast cancer biopsies.

Results are shown in FIG. 5. Akt3, not Akt1 and Akt2, show strong correlation with EMT and stem markers in breast cancer cell lines and breast cancer biopsies.

Example 6 Knocking Down Akt3 is Able to Reverse EMT and CSC Traits in Breast Epithelial Cells MCF10A cells and MDA-MB 231 cells were cultured as described in Example 1 and 3. MCF10a were transduced with the EMT driver "Slug" (Slug/control) as described in Example 1. siRNA-mediated silencing of Akt3 was done using HiPerFect transfection reagent (Qiagen) according to the manufacturer's protocol, and the cells were cultured for 2-3 days. Annealed siRNAs against Akt3 ("sIAKT3"; HsAkt3_2 HP), and GAPDH ("control"; Hs_GAPDH_3) were used at 60 nM final concentrations (all were from Qiagen). SDS/PAGE, Immunoblotting and antibodies as described in Example 1 except Rat anti-human Vimentin (MAB2105; R&D Systems). The 3D matrigel experiments were performed as described (Gjerdrum C, Tiron C, Høiby T, Stefansson I, Haugen H, Sandal T, Collett K, Li S, McCormack E, Gjertsen B T, Micklem D R, Akslen L A, Glackin C, Lorens J B. Axl is an essential epithelial-to-mesenchymal transition-induced regulator of breast cancer metastasis and patient survival. Proc Natl Acad Sci USA. 2010 Jan. 19; 107(3):1124-9.). The cells were visualized by fluorescence microscopy (DAPI nuclear stain) using a Nikon TE2000 microscope (Nikon).

Figure 6:
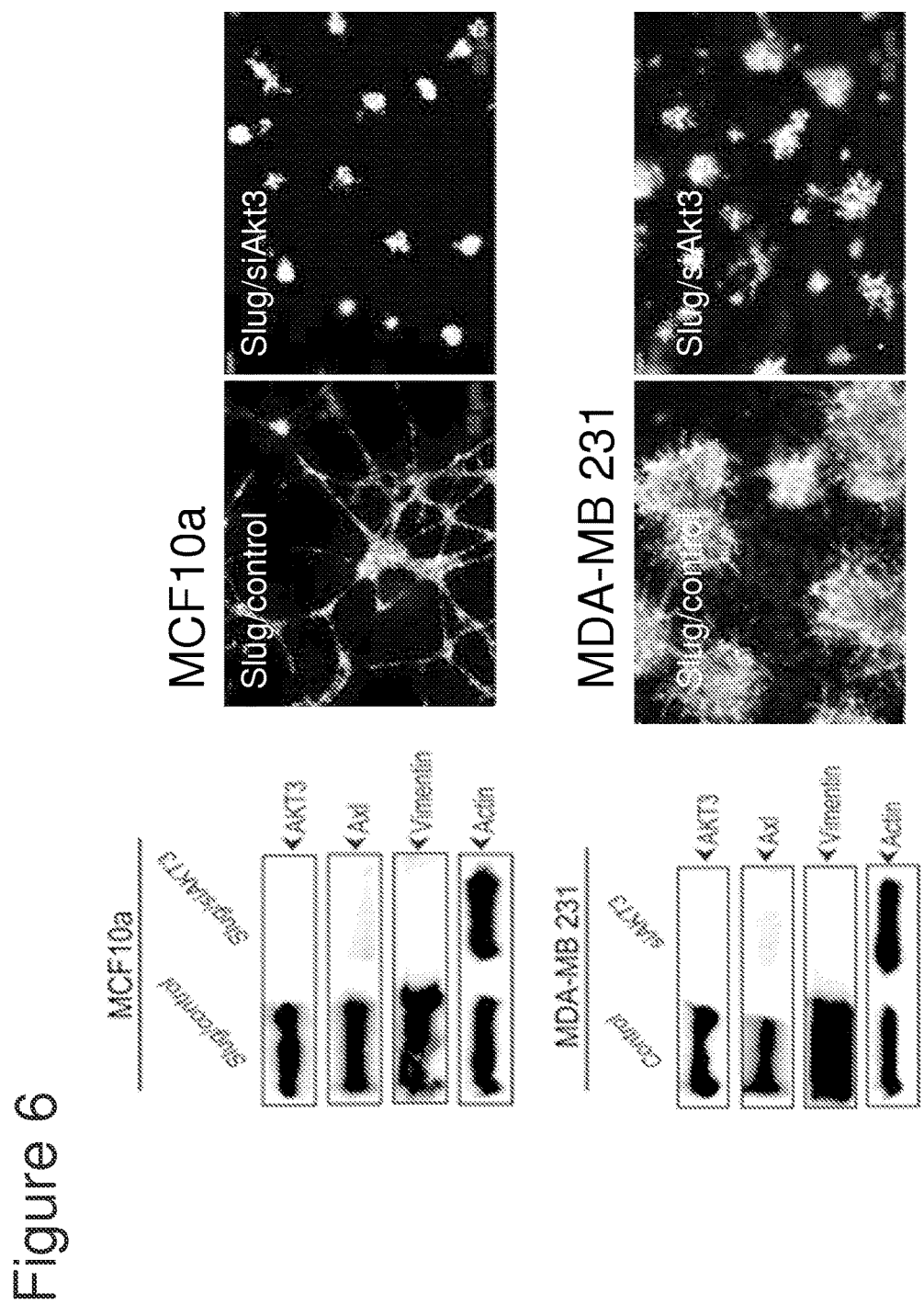
FIG. 6 shows suppression of Akt3 expression is able to reverse EMT and CSC traits in breast epithelial cells.

These data, presented in FIG. 6, show that knocking down Akt3 is able to reverse EMT traits in two different breast epithelial cells as shown by down-regulation of the mesenchymal marker Vimentin, and inhibition of invasive, stellate growth in 3D Matrigel.

Example 7 Constitutively Active Akt3, but not Constitutively Active Akt1 is Able to Activate EMT and to Activate EMT Regulators SDS/PAGE, Immunoblotting and antibodies as described in Example 1 and 6, except Rabbit anti-human N-cadherin (ab18203; Abcam), Rabbit anti-human Ecadherin (24E10; Cell Signaling), Rabbit anti-human β-catenin (L54E2; Cell Signaling), Mouse anti-human Twist (Twist2C1a; Abcam).

MCF10A cells, cultured as described in Example 1, were transduced with empty vector (CRU5-IRES-GFP described in Example 1), or the CRU5-IRES-GFP vector harboring a constitutively active myristylated form of Akt1 (myrAkt1) or a constitutively active myristylated form of Akt3 (myrAkt3). When directed to membranes by the addition of a sre myristoylation sequence, Akt becomes constitutively active (Barthel A, Kohn A D, Luo Y, Roth R A. A constitutively active version of the Ser/Thr kinase Akt induces production of the ob gene product, leptin, in 3T3-L1 adipocytes. Endocrinology. 1997 August; 138(8):3559-62). MCF10A cells were transduced with either retroviral vector "myr-AKT1" or with a retroviral vector "myr-AKT3". Control cells ("wt") were transduced with neither vector. Immunoblots of proteins extracted from these cell lines were probed with a panel of markers associated with epithelial and mesenchymal cell fates and EMT.

Figure 7:
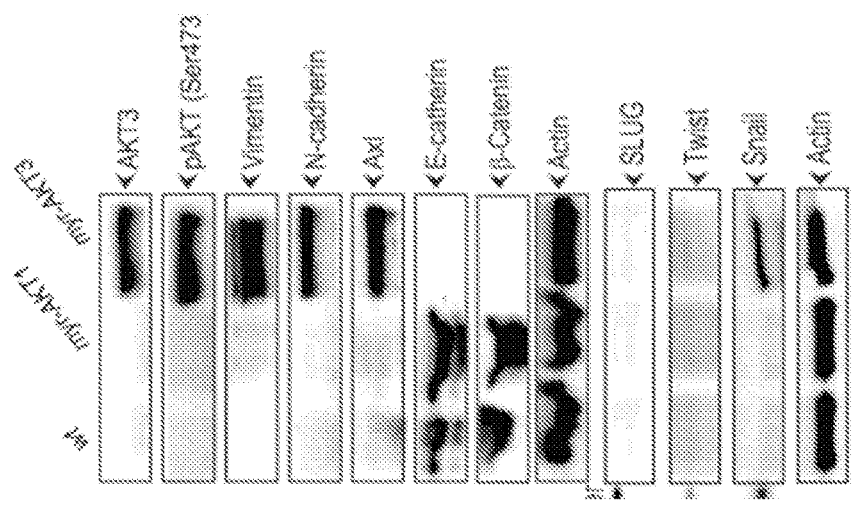
FIG. 7 is a photograph of gel experiments on the activity of Akt isoforms.
Figure 8:
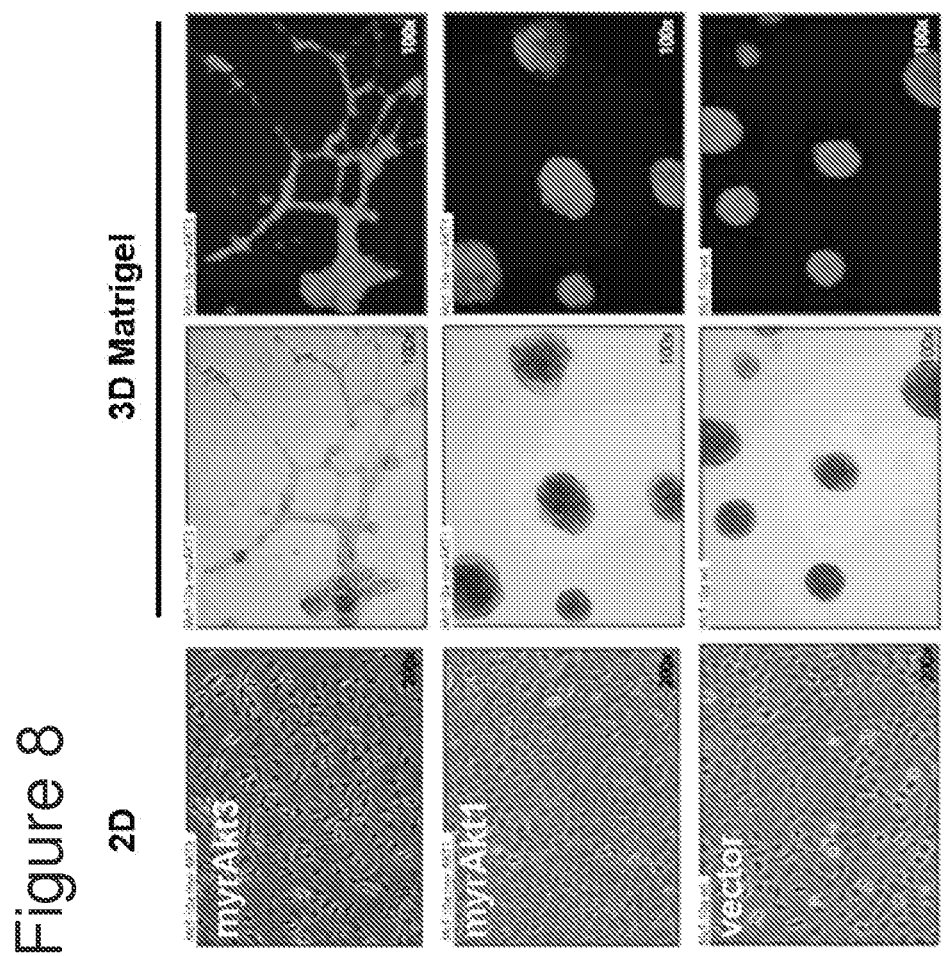
FIG. 8 is a photograph of growth studies of breast cancer cells.

These data, shown in FIG. 7, unexpectedly show that constitutively active Akt3, but not constitutively active Akt1 is able to activate EMT as shown by up-regulation of mesenchymal markers (N-cadherin, Vimentin) and loss of epithelial markers (E-cadherin, b-catenin). The expression of myr-Akt3 also leads to activation of the EMT regulators Snail and Axl, and phosphorylation of Akt suggesting the existence of a positive feedback loop.

Example 8 Constitutively-Active, Akt3 (MyrAkt3), but not Constitutively-Active Akt1 is Able to Induce EMT and CSC Traits in Breast Epithelial Cells MCF10A cells were used in this experiment along with a retroviral vector ("myr-Akt1") driving expression of constitutively active Akt1 and a retroviral vector ("myr-AKT3") driving expression of constitutively active Akt3. The 3D matrigel experiments were performed as described in Example 6. The cells were visualized at indicated magnification by phase-contrast and fluorescence microscopy (DAPI nuclear stain) using a Nikon TE2000 microscope (Nikon).

Results shown in FIG. 5. These data show that constitutively-active Akt3, but not constitutively-active Akt1 is able to induce EMT and CSC traits in breast epithelial cells (fibroblastoid cell growth in 2D culture and invasive, stellate growth in 3D Matrigel).

Figure 9:
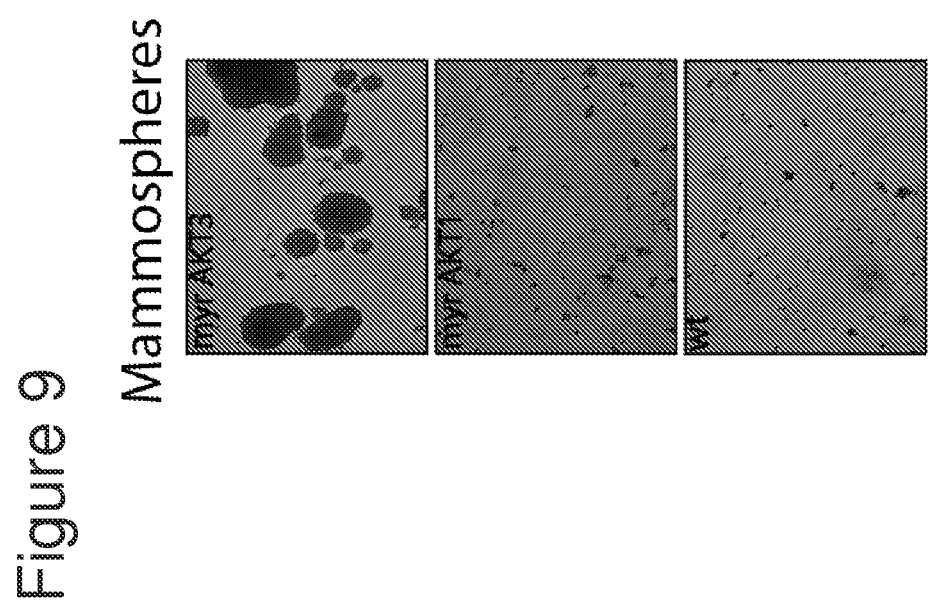
FIG. 9 is a set of photographs of mammosphere cultures of breast cancer cells and a graph.

Example 9 Cells Expressing Constitutively Active Akt3, but not Cells Expressing Constitutively Active Akt1 Show the Ability to Grow in Mammospheres Cell lines used are as described in Example 1. Mammosphere culture of MCF10A cells was performed as described (Down G, Abdallah W M, Foley J M, Jackson K W, Clarke M F, Kawamura M J, Wicha M S. In vitro propagation and transcriptional profiling of human mammary stem/progenitor cells. Genes Dev. 2003 May 15; 17(10):1253-70). Briefly, single cells were plated on 35 mm ultra-low attachment plates (Corning, USA, Cat, #3473), 20000 viable cells/ml at a total of 30000 cells per well. The mammospheres were cultured for 10 days, imaged and mammospheres quantified using ImageJ (http://rsbweb.nih.gov/ij/index.html). Statistical analyses were based on Students t-test. Results shown in FIG. 9.

The ability to form mammospheres—large structures composed of many cells—is considered to be a trait of cancer stem cells. MCF10A cells expressing constitutively-active Akt3 were able to form as mammospheres. In contrast cells expressing constitutively active Akt1 and untreated MCF10A cells are not able to form mammospheres. The ability to form mammospheres is therefore triggered by signalling through Akt3 rather than through Akt1.

Example 10 Constitutively-Active Akt3 (myr-Akt3), but not Constitutively-Active Akt1 is Able to Induce EMT, Leading to a Rise in EMT/Mesenchymal Markers (Axl, Vimentin, N-Cadherin) and Loss of Epithelial Markers (E-Cadherin)

HMLER cells were transduced with retroviral vectors that express myrAkt1 or myrAkt3 as described in Example 8 and analyzed for Axl receptor protein, epithelial (E-cadherin) and mesenchymal (vimentin, N-cadherin) marker expression. Akt1/3 and pAkt levels as described in Example 7.

Figure 10:
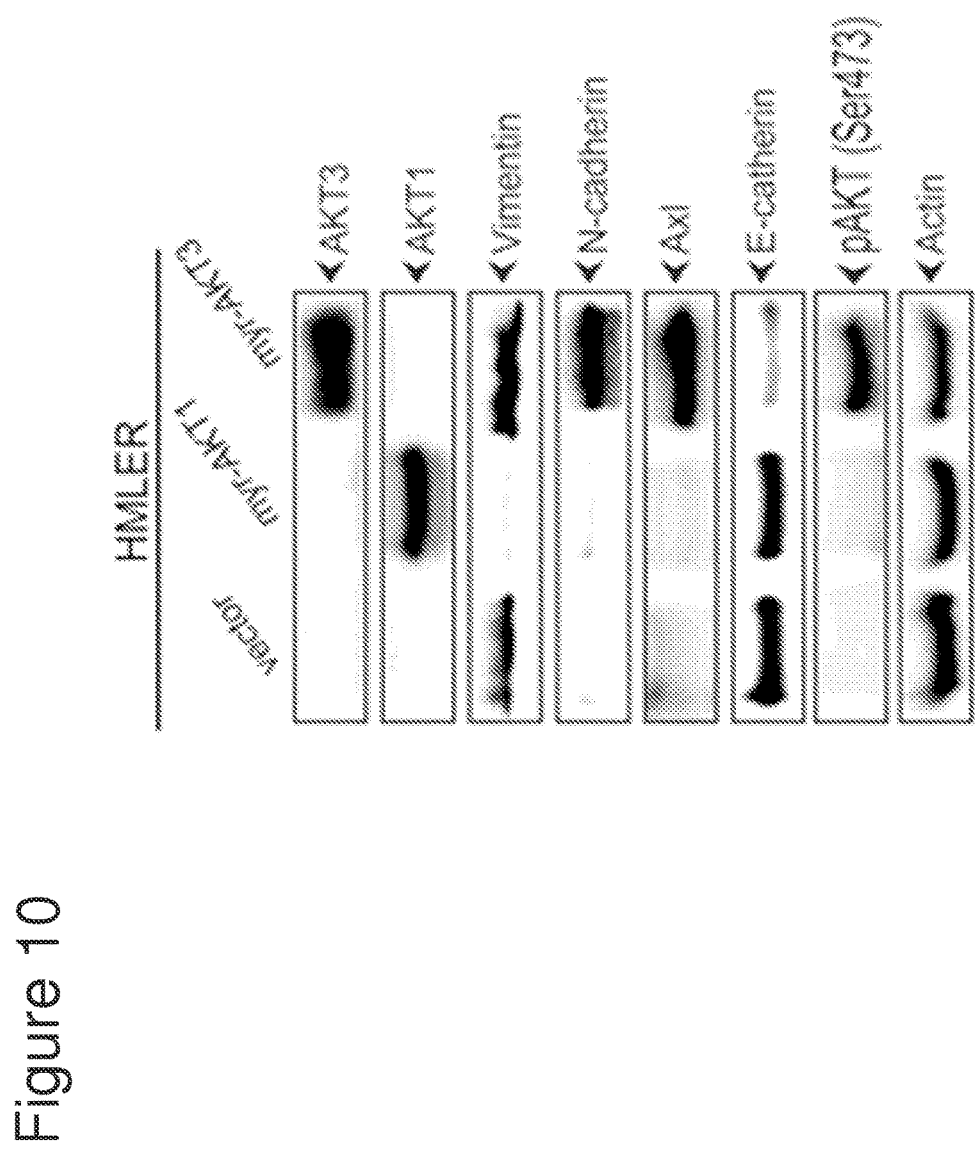
FIG. 10 shows constitutively-active Akt3 (myr-Akt3), but not constitutively-active Akt1 is able to induce EMT.

The results are shown in FIG. 10. Constitutively active Akt3, but not constitutively active Akt1 is able to activate EMT and to activate EMT regulators.

Example 11 Constitutively-Active Akt3 (MyrAkt3), but not Constitutively-Active Akt1 is Able to Induce EMT and CSC Traits in Breast Epithelial Cells HMLER cells expressing myrAkt1, myrAkt3 or empty vector were grown in 2D (Left) and 3D Matrigel (Right), and visualized by phase contrast microscopy as described in Example 8.

Figure 11:
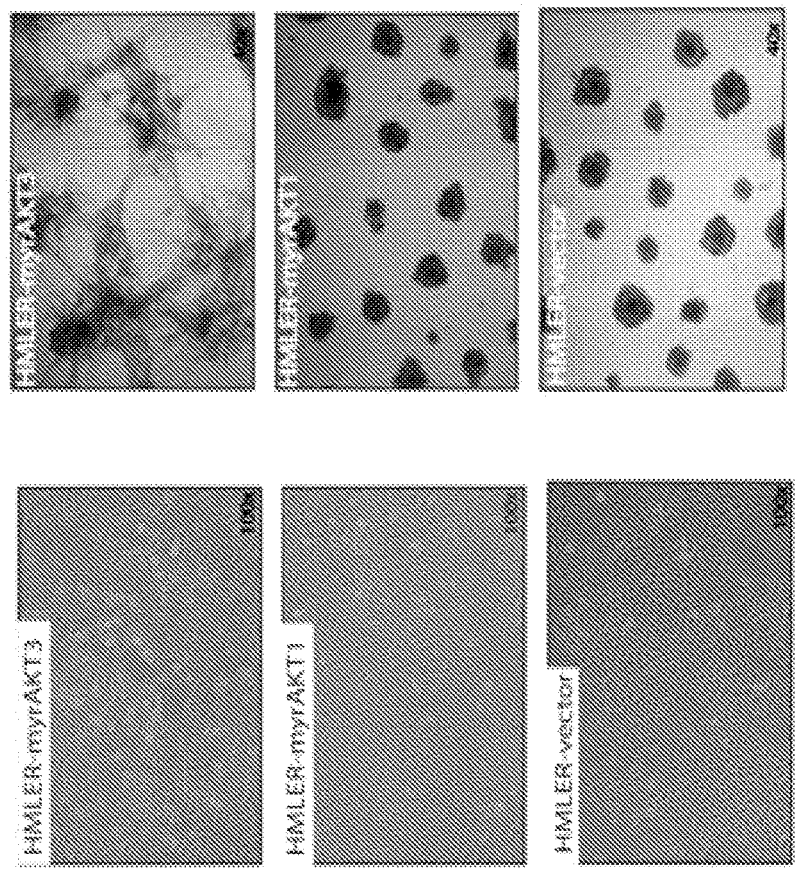
FIG. 11 shows constitutively-active Akt3 (MyrAkt3), but not constitutively-active Akt1 is able to induce EMT and CSC traits in breast epithelial cells.

Results shown in FIG. 11.

HMLER cells typically have epithelial morphology (sheets of rounded cells) when grown on tissue culture plastic (Left), and are not invasive when grown embedded in matrigel (Right). These data show that constitutively-active Akt3, but not constitutively-active Akt1 is able to induce EMT and CSC traits in transformed breast epithelial HMLER cells (fibroblastoid cell growth in 2D culture and invasive, stellate growth in 3D Matrigel).

Example 12 Cells Expressing Constitutively Active Akt3, but not Cells Expressing Constitutively Active Akt1 Show the Ability to Grow in Mammospheres HMLER cells expressing myrAkt1, myrAkt3 were grown in mammosphere culture and quantified as described in Example 9.

Figure 12:
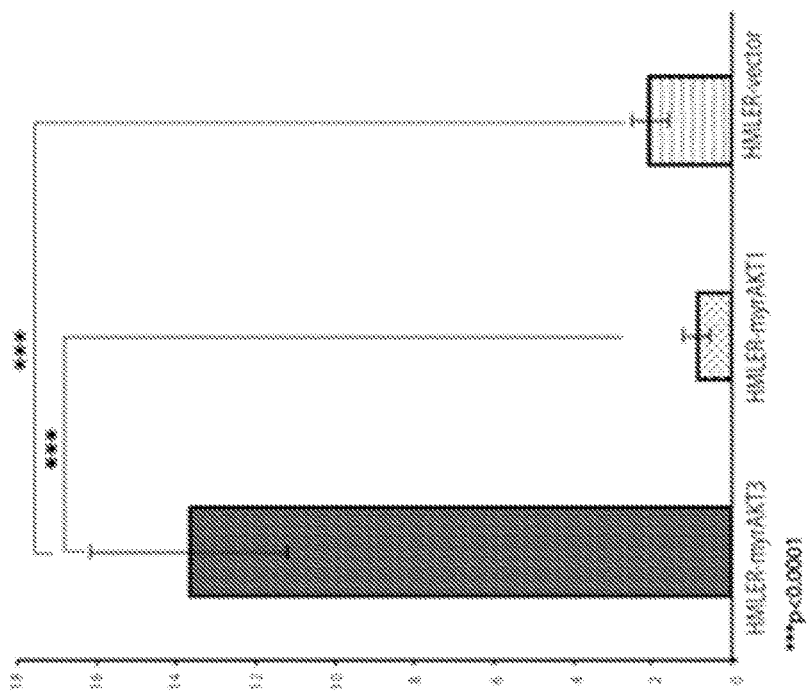
FIG. 12 shows cells expressing constitutively active Akt3, but not cells expressing constitutively active Akt1 show the ability to grow in mammospheres.

The results are shown in FIG. 12.

Tumorsphere formation is a characteristic of cancer stem cells. HMLER cells are normally not able to form mammospheres, indicating a lack of cancer stem cell characteristics. Transfection with a vector encoding activated Akt3 (myrAkt3) but not with a vector encoding activated Akt1 (myrAkt1) confers the ability to form mammospheres.

Example 13 Cells Expressing Constitutively Active Akt3 Show a Much Higher Ability to Form Tumors than Cells Expressing Constitutively Active Akt1

HMLER cells transduced with retroviral vectors "HMLER/vector", "HMLER/myrAkt1" and "HMLER/myrAkt3" as described in Example 10, were injected into host mice at limiting dilutions as described (Mani S A, Gun W, Liao M J, Eaton E N, Ayyanan A, Zhou A Y, Brooks M, Reinhard F, Zhang C C, Shipitsin M, Campbell L L, Polyak K, Brisken C, Yang J, Weinberg R A. The epithelial-mesenchymal transition generates cells with properties of stem cells. Cell, 2008 May 16; 133(4):704-15).

Results presented in FIG. 13. These data show that expressing constitutively active Akt3 (HMLER/myrAkt3) significantly increases the HMLER cell ability to form tumors, compared to control cells or cells expressing constitutively active Akt1 (see number of tumors formed at 1000 cells seeded).

Figure 14:
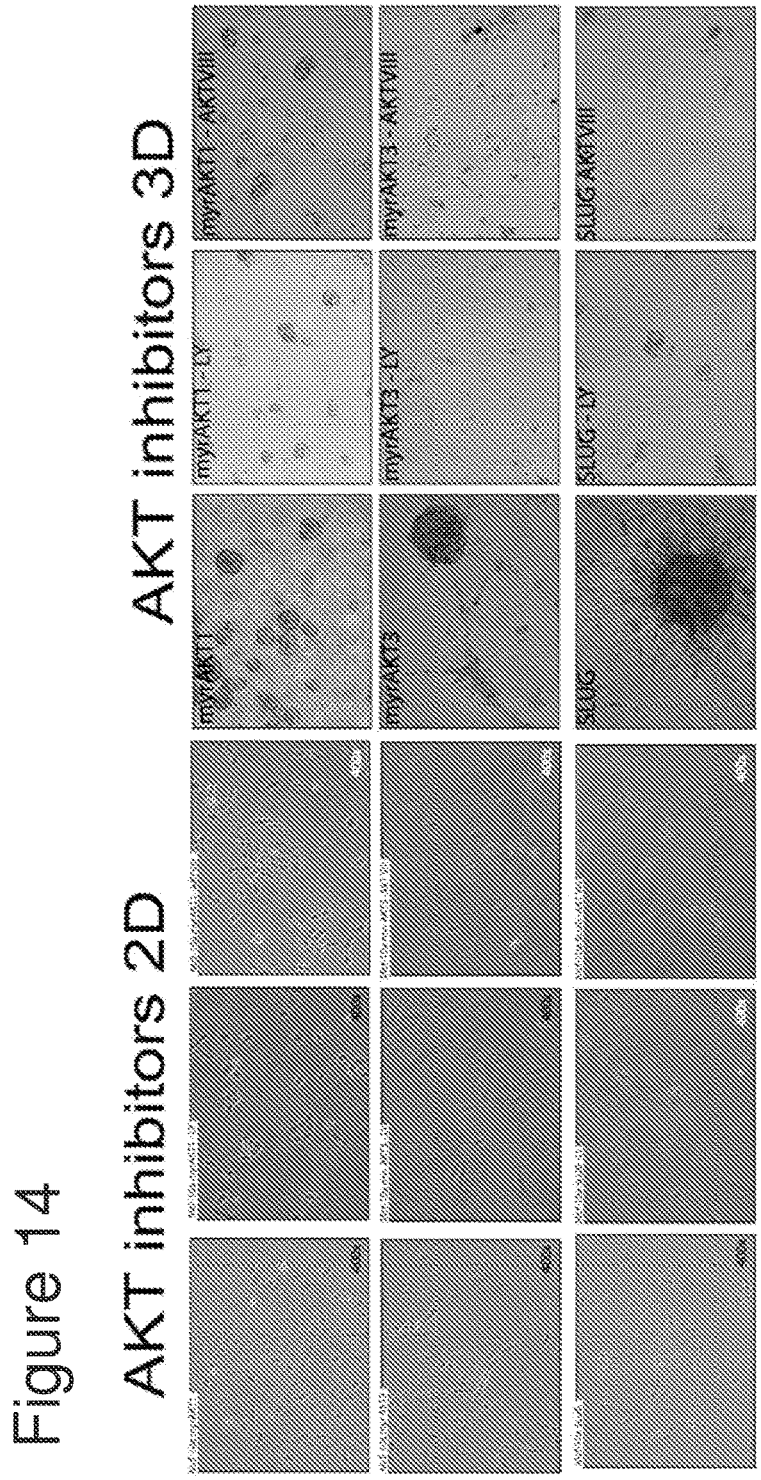
FIG. 14 is a photograph of growth studies of breast cancer cells.

Example 14 Constitutively Active Akt3 and Slug, but not Constitutively-Active Akt1 is Able to Induce the Mesenchymal Phenotype and Invasive Growth; Akt Inhibitors Inhibit the Mesenchymal Phenotype MCF10A cells were cultured and transduced with retroviral constructs expressing myrAkt1, MyrAkt3 or Slug as described in FIGS. 1 and 3. The cells were treated with Akt inhibitors LY294002 (10 µM, Cell Signaling Technology, Cat. #9901) and Akt VIII (10 µM, Merck, Cat. #124018) for 12 hours as indicated. Cells were then either visualized at indicated magnification by phase-contrast microscopy, or seeded for invasive growth in 3D Matrigel as described in Example 3. Results shown in FIG. 14.

These results show that constitutively-active Akt3 and Slug, but not constitutively-active Akt1 is able to induce the mesenchymal phenotype in 2D growth and invasive growth in 3D growth matrigel. Akt inhibitors LY-294002 and AKT VIII inhibit the mesenchymal phenotype induced by Akt3, but also the mesenchymal/invasive phenotype induced by Slug in 2D and 3D growth, suggesting that Akt3 is required for Slug signalling.

Example 15 Constitutively-Active Akt3 and Slug, but not Constitutively-Active Akt1 is Able to Activate EMT and Akt Inhibitors are Able to Partially Reverse the Mesenchymal Phenotype MCF10A cells were cultured and transduced with retroviral constructs expressing myrAkt1, MyrAkt3 or Slug as described in FIGS. 1 and 3. The cells were treated with Akt inhibitor as described in FIG. 6. SDS/PAGE, immunoblotting and antibodies as described in Examples 1 and 4.

Figure 15:
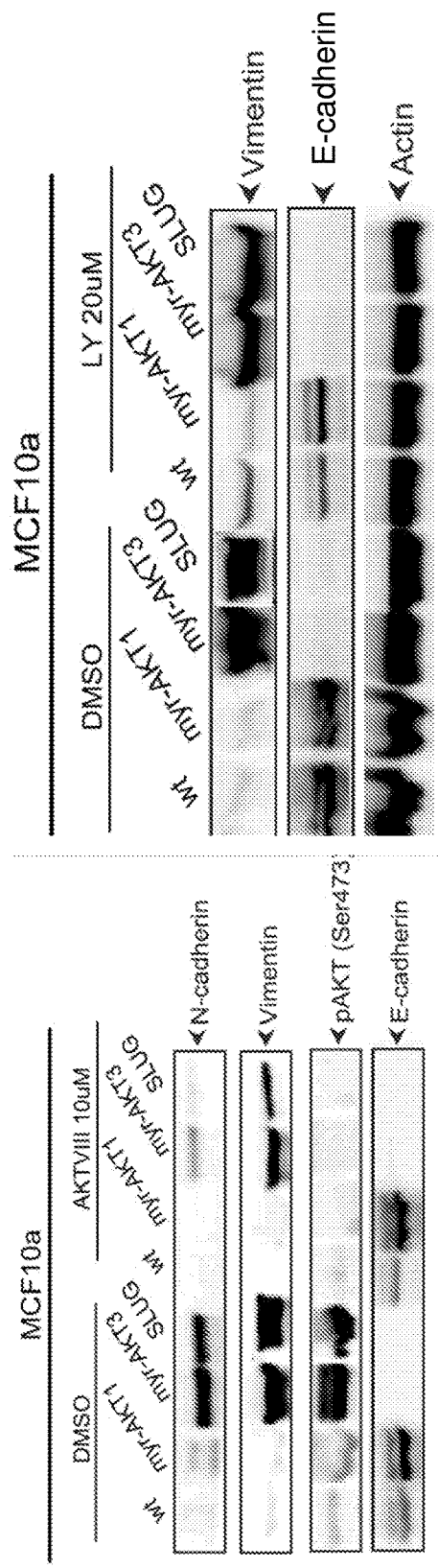
FIG. 15 is an image of a gel from experiments in which breast cancer cells were treated with an Akt inhibitor.

Results are shown in FIG. 15.

These results show that constitutively-active. Akt3 and Slug, but not constitutively-active Akt1 is able to activate EMT as shown by up-regulation of the markers N-cadherin, vimentin and loss of the epithelial marker E-cadherin. The Akt inhibitor AKT VIII (Left) is able to fully inhibit Akt activation (pAkt) and partially reverse the mesenchymal phenotype, as shown by significant reduction of the mesenchymal markers N-cadherin and vimentin (Left). The Akt inhibitor LY-294002 similarly shows partial inhibition of EMT, showing reduced vimentin expression. Neither inhibitor led to re-expression of the epithelial marker E-cadherin.

Example 16 RNAi Silencing of Akt3, but not Silencing of Akt1 in MCF10A Cells Induced to Undergo EMT (by Expression of H-RasV12 or Slug) Significantly Reduces P-Akt Levels MCF10A cells were transduced with retroviral vectors encoding EMT inducers Slug, and H-RasV12. From these cells small interfering RNA-mediated silencing was done using HiPerFect transfection reagent (Qiagen) according to the manufacturer's protocol and the cells were cultured for 3 days. Annealed siRNAs against Akt1 (Hs_AKT1-_5 Flexitube siRNA), Akt3 (Hs_AKT3_2 HP siRNA) and GAPDH (Hs_GAPDH_3 HP validated siRNA) (all from Qiagen) as a negative control were used at 60 nM final concentrations. After silencing, cells were lysed with SDS-PAGE loading buffer, sonicated and boiled. Lysates were subjected to Western blot analysis and blots were probed using Akt1, Akt3, pAkt Ser473 antibodies as described in FIG. 2 and α-tubulin 12g10 (Hybridoma Bank; http://dshb.biology.uiowa.edu/12G10-anti-alpha-tubulin).

Figure 16:
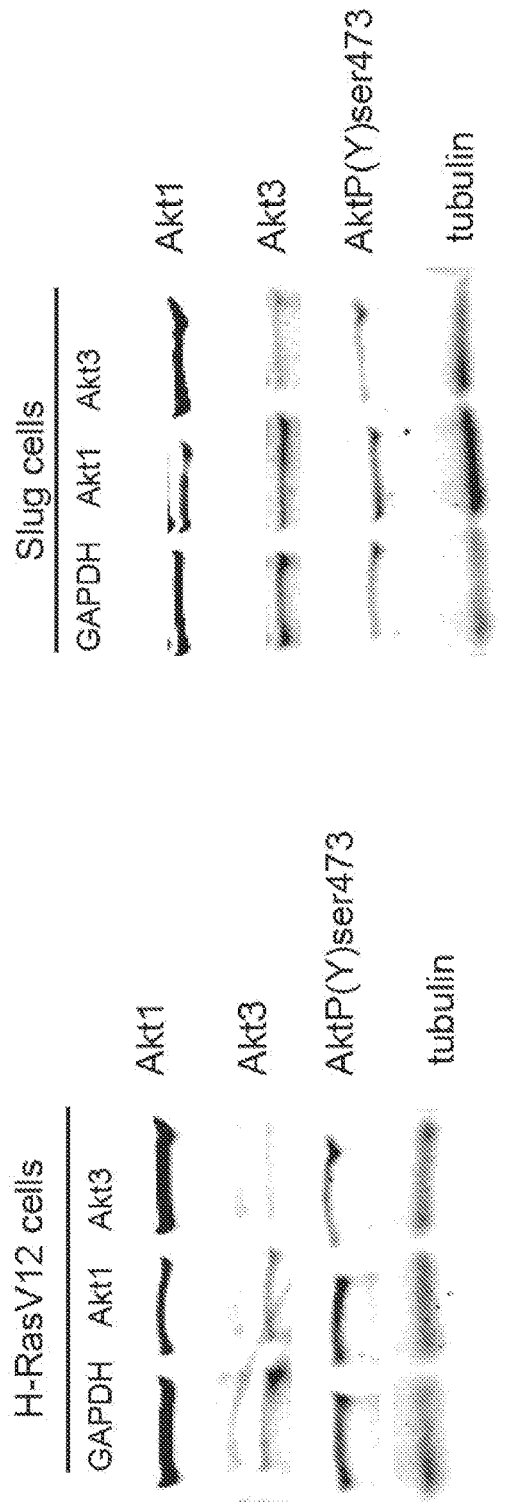
FIG. 16 is a photograph of gels from experiment to study activity of Akt isoforms.

These results are presented in FIG. 16. These results show that knocking down the level of Akt3, but not knocking down the level of Akt1 in cells induced to undergo EMT is able to significantly reduce the level of total P-Akt. This suggests that phospho-Akt3 represents the major pAkt isoform in EMT-induced MCF10A cells.

Example 17 Constitutively Active Akt3, but not Constitutively Active Akt1 is Localized to the Cell Nucleus HMLER cells were cultured as described in Example 2, and SDS/PAGE, Immunoblotting and antibodies as described in Example 1 except anti-histone 3 (Cell Signaling, Histone H3 Antibody #9715). Nuclear extraction was done according to manufacturer' instructions (Universal Magnetic Co-IP Kit, Active Motif, 54002). Immunofluorescence staining of constitutively active Akt1 and Akt3 of fixated cells were done using antibodies as in Example 1, by the method described by the manufacturer (Cell Signaling, Immunofluorescence General Protocol).

Figure 17:
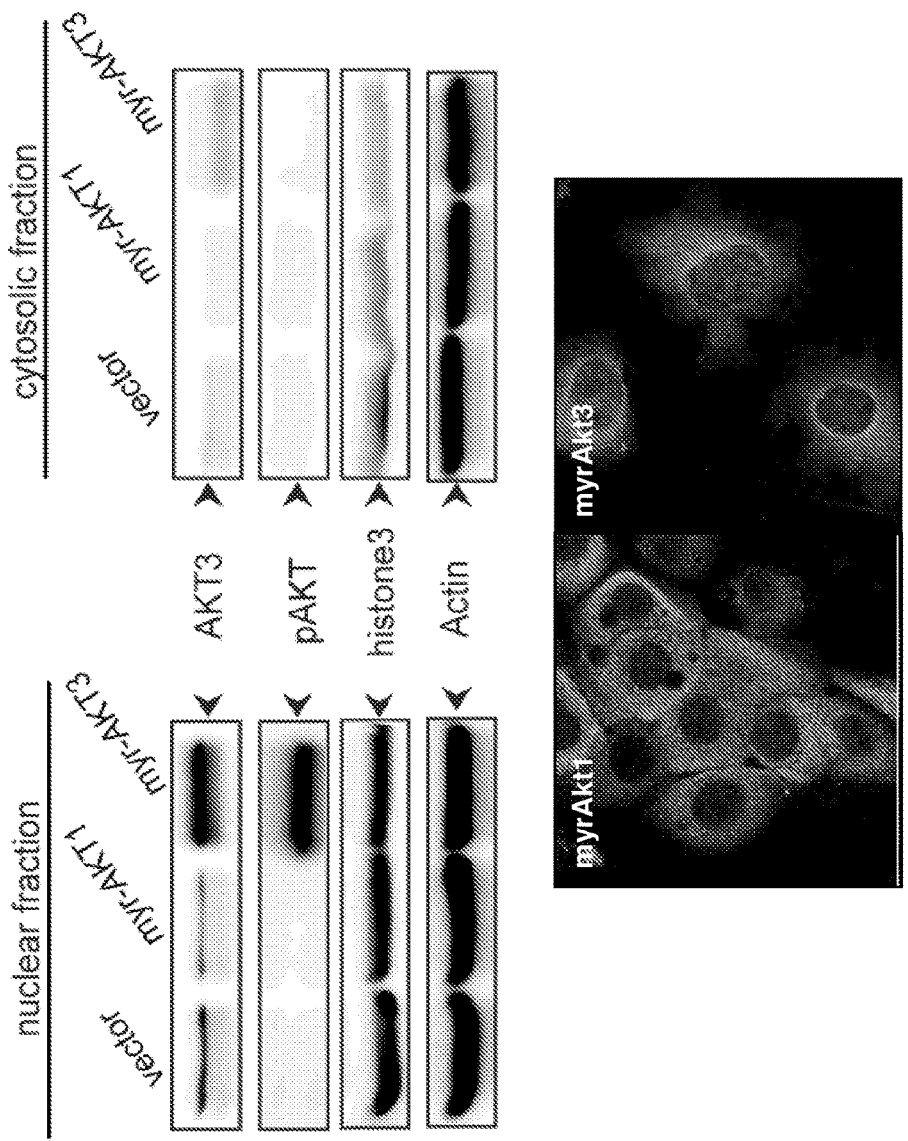
FIG. 17 shows constitutively active Akt3, but not constitutively active Akt1 is localized to the cell nucleus

These results are presented in FIG. 17. Activated Akt3 (MyrAkt3) localizes to the nuclear fraction in HMLER cells (top). Immunofluorescence staining reveals nuclear/perinuclear staining for myrAkt3 but exclusion from the nucleus for myrAkt1.

Example 18 Akt3 and the Transcription Factor Snail are Found Overwhelmingly in the Nuclear Fraction of Cultured Triple-Negative Breast Cancer Cells. Tubulin (Cytoplasmic) and Lamin (Nuclear) Markers Confirm Successful Fractionation MDA-MB 231 cells were cultured as described in Example 3. SDS/PAGE, Immunoblotting and antibodies as described in Examples 1 and 16, exept Laminin A/C from Santa Cruz, sc-7292. Cytosolic and nuclear proteins were isolated as described in Example 17.

Figure 18:
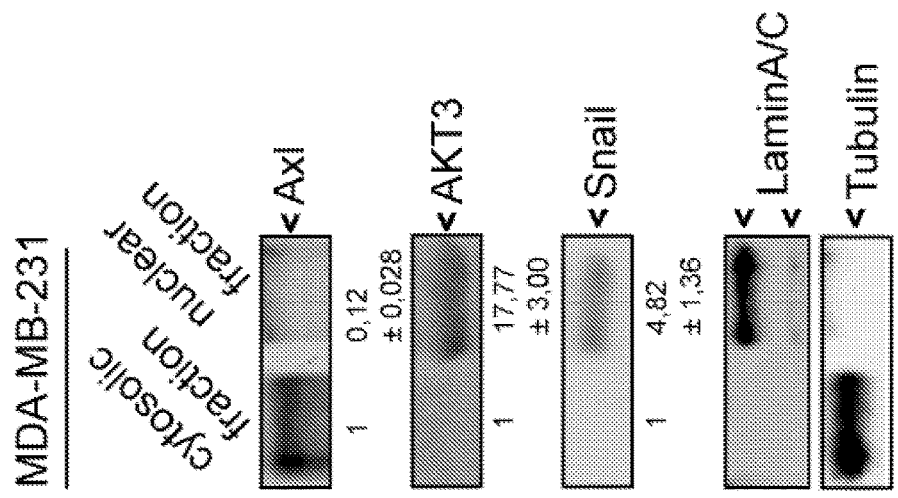
FIG. 18 shows Akt3 and Snail are found in the nuclear fraction

The results of these experiments are shown in FIG. 18. As expected, the transcription factor Snail is found in the nucleus. Unexpectedly, Akt3 was also almost exclusively nuclear.

Figure 19:
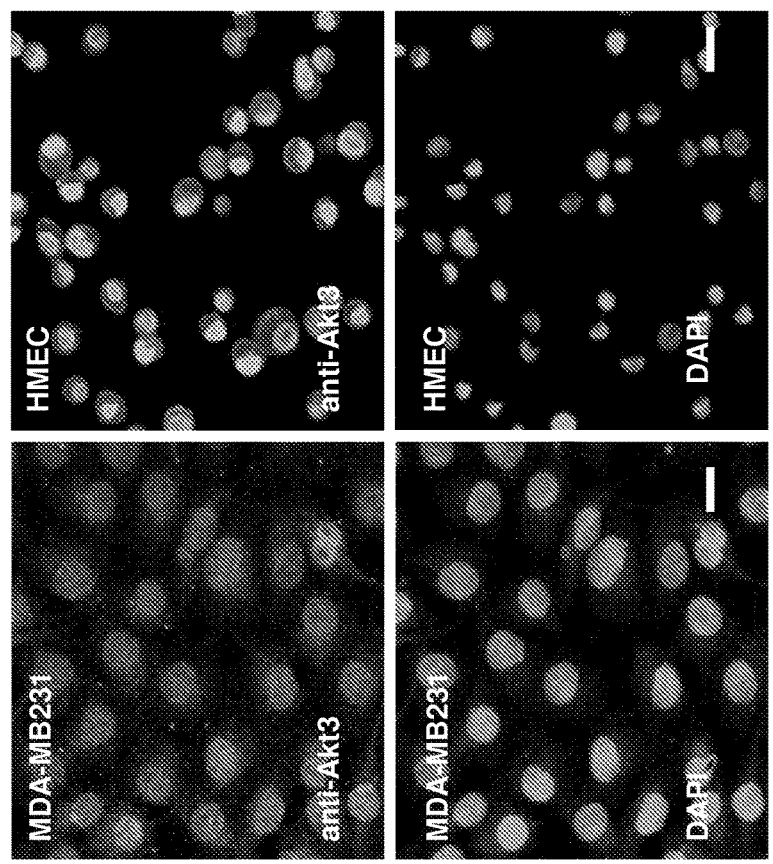
FIG. 19 shows Akt3 localizes to the nucleus in cultured triple negative breast cancer cells and primary human mammary epithelial cells

Example 19 Akt3 Localizes to the Nucleus in Cultured Triple Negative Breast Cancer Cells and Primary Human Mammary Epithelial Cells Culturing of MDA-MB-231 cells was as described in Example 3. Primary human mammary epithelial cells (HMEC) were isolated as described (Garbe J C, Pepin F, Pelissier F A, Sputova K, Fridriksdottir A J, Guo D E, Villadsen R, Park M, Petersen O W, Borowsky A D, Stampfer M R, Labarge M A. Accumulation of multipotent progenitors with a basal differentiation bias during aging of human mammary epithelia. Cancer Res. 2012 Jul. 15; 72(14):3687-701) Localization of Akt3 (anti-Akt3-FITC, top panels) in MDA-MB-231 and primary human mammary epithelial cells (HMEC) as in Example 17. Nucleus was stained by DAPI (lower panels). Bar: 50 micron The results of these experiments are shown in FIG. 19. Akt3 protein (top panels) is localized to the nuclei (compare to nuclear stain, bottom panels) in both breast cancer cells and primary mammary epithelial cells.

Example 20 Knocking Down Axl Kinase Significantly Reduces EMT Induced Nuclear Localization of Akt3

HMLER and HMLER/Slug cells were transduced retroviral vectors that express Axl-targeting shRNA (shAxl2) or control luciferase shRNA (shLuc). Cytoplasmic and nuclear cell fractions were isolated as described in Example 17, and Akt3 protein level were measured by Immunoblotting in nuclear and cytoplasmic cell fractions. Immunofluorescence of transduced cells (GFP, cytoplasmic green) stained with anti-Akt3-FITC (nuclear green) or DAPI nuclear stain.

Figure 20:
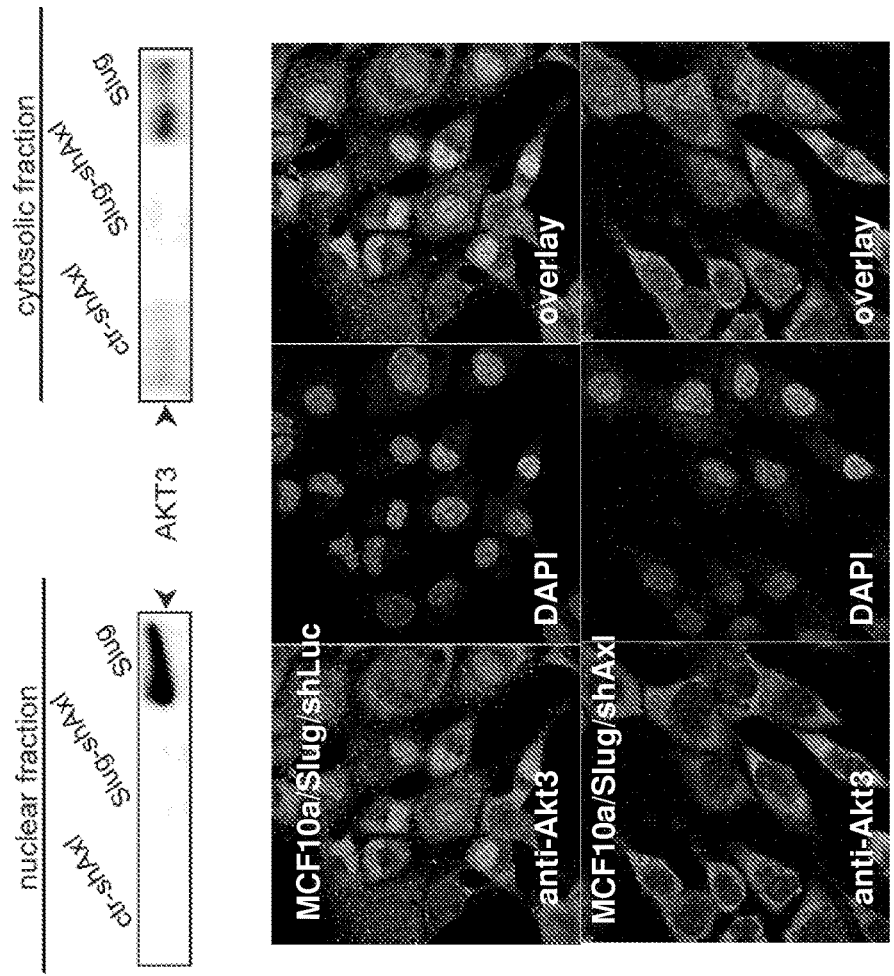
FIG. 20 shows suppression of Axl kinase expression reduces EMT induced nuclear localization of Akt3

Resuts from this experiment in FIG. 20. Induction of EMT by Slug leads to nuclear localization of Akt3 in an Axl-dependent process.

Example 21 Inhibition of Axl Kinase Activity Inhibits Nuclear Localization of Akt3

Quantification of nuclear Akt3 immunofluorescence (anti-Akt3-FITC, top panels) in mammary epithelial cells (HMEC) treated with vehicle (DMSO), cKit TKI (1 uM imatinib) and Axl TKI (600 nM BGB324). Bar: 50 micron, *$P<0.05$.

Figure 21:
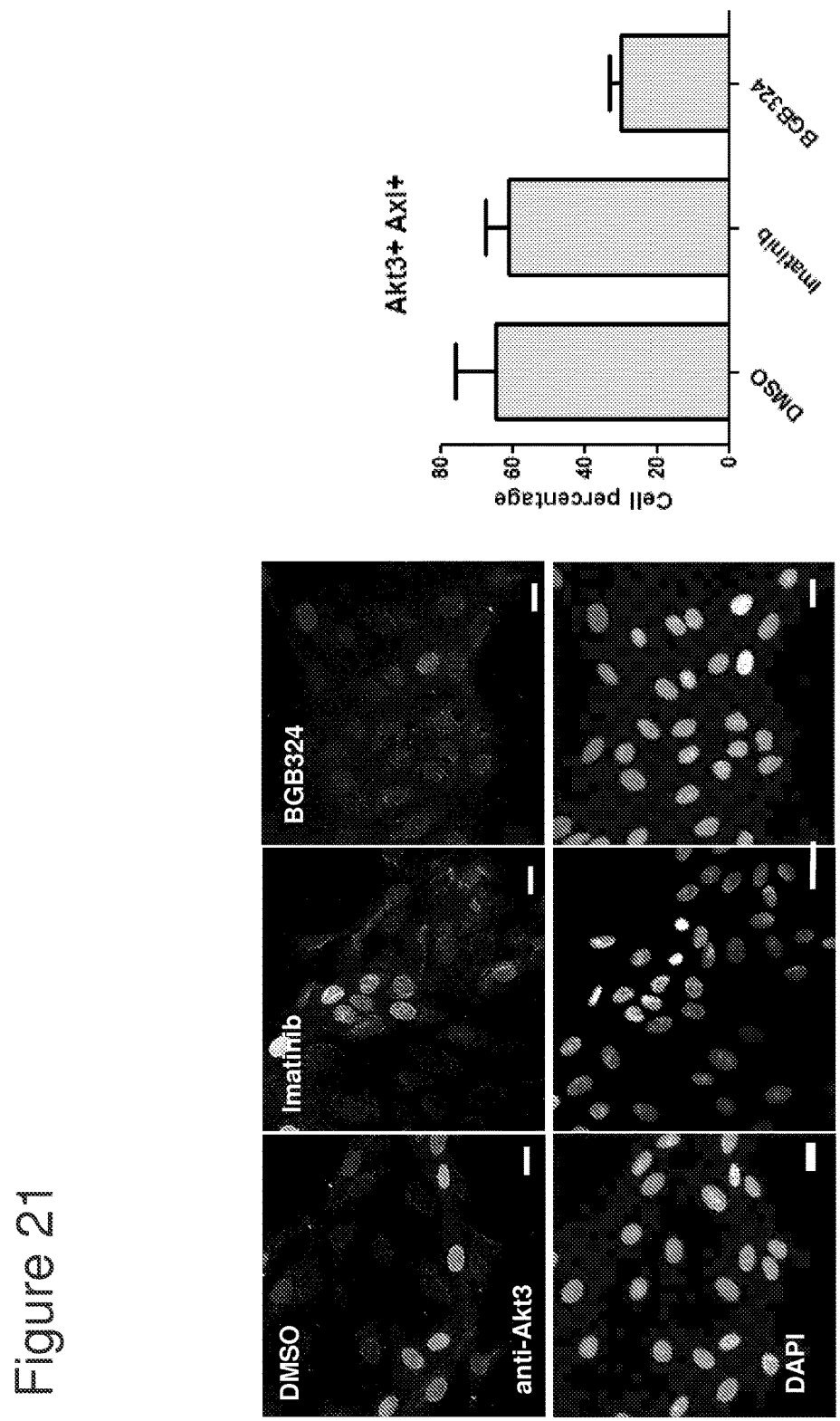
FIG. 21 shows inhibition of Axl kinase activity inhibits nuclear localization of Akt3

Results presented in FIG. 21 show that blocking Axl activity (BGB324) inhibit Akt3 nuclear localization, while inhibiting cKit (Imatinib) has no effect on Akt3 nuclear localization.

Example 22 Akt1 and Akt3 Kinases are Able to Directly Phosphorylate Snail Protein in a Biochemical Assay Containing no Other Proteins SNAI1/Snail coding sequence were cloned into the pGEX-421-1 vector (Promega) and sequence verified. GST fusion protein were expressed in Escherichia coil (Rosetta BL21DE3) and purified according to the manufacturer's instructions (BD Biosciences); the GST moiety was cleaved by using thrombin. In vitro kinase assays were performed using recombinant Akt1 and Akt3 (ProQinase GmbH), Snail and Slug substrate proteins, and $^{32}$P-ATP and detected by autoradiography as described (Tuomi et al., 2009).

Figure 22:
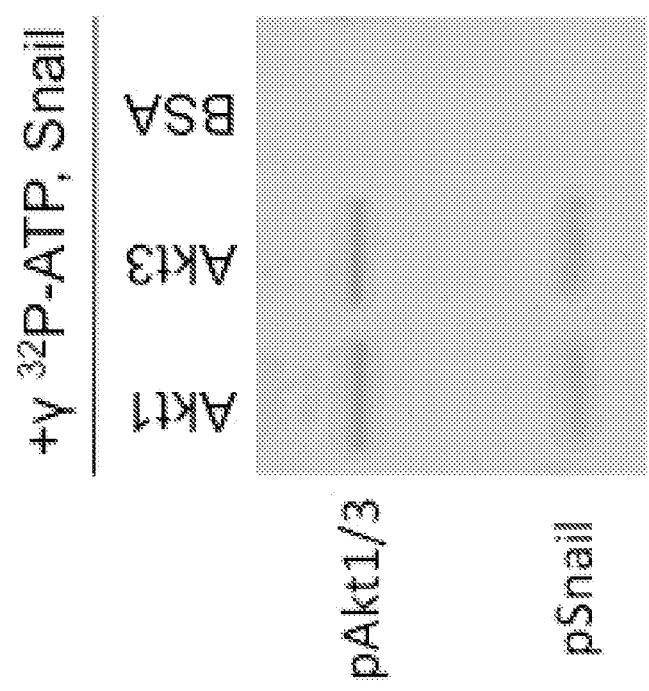
FIG. 22 shows Akt1 and Akt3 kinases are able to directly phosphorylate Snail protein

Results presented in FIG. 22 show that Akt1 and Akt3 kinases are able to directly phosphorylate Snail protein In a biochemical assay containing no other proteins.

Example 23 The SureFire Assay Detects Phospho-Akt3 in Insulin-Stimulated Melanoma Cells (WM115) that Express Akt3. No Signal is Detected in Breast and Prostate Canines that Express Akt1 and Akt2 but not Akt3 (MCF7 and LNCaP)

A SureFire assay was used to specifically detect activated (phosphorylated) Akt3 in WM115, MCF7 and LNCaP cells. Briefly cells were lysated, and antibodies recognizing phosphorylated Akt (p473) and Akt3 were coupled to acceptor and donor beads as described by the manufacturer (PerkinElmer). Cells were either unstimulated or stimulated with 10 nM insulin for 10 minutes to activate Akt.

Figure 23:
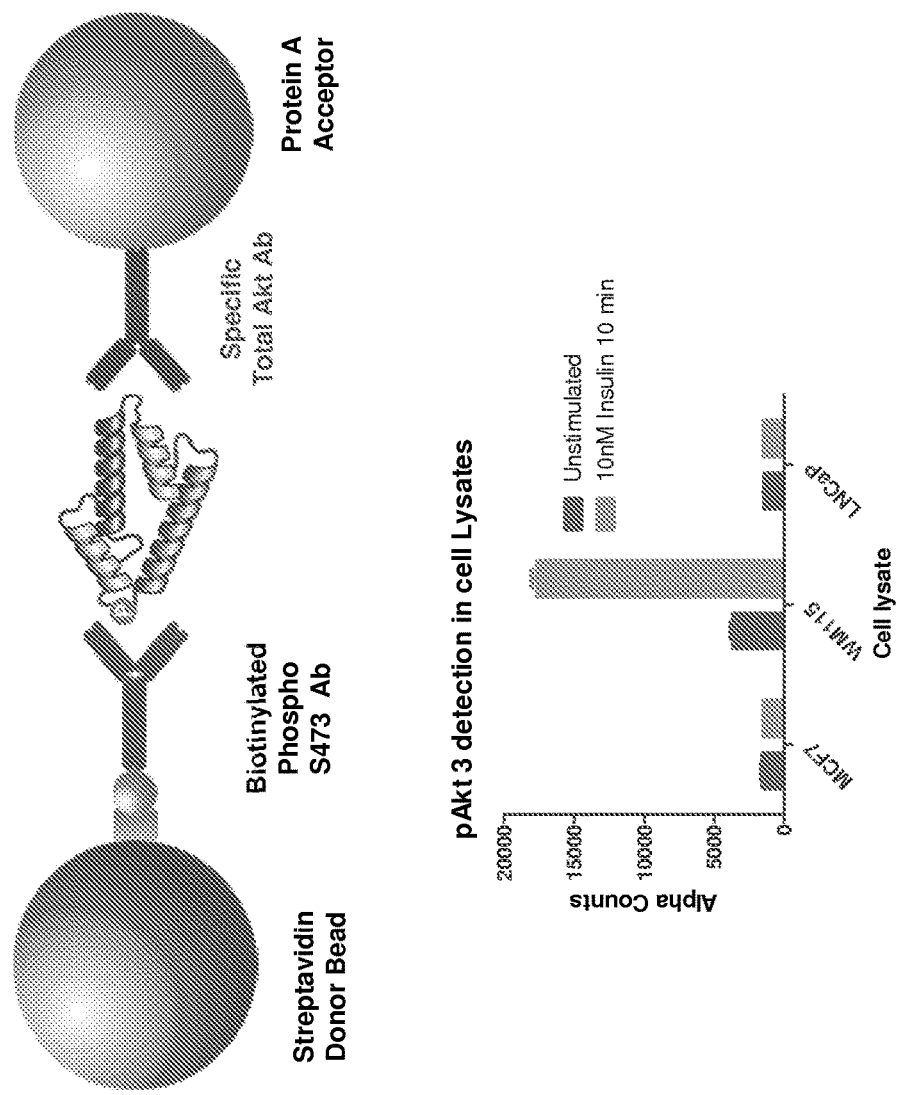
FIG. 23 shows specific detection of phospho-Akt3 in MCF7, WM115 and LNCaP cells

The results of these experiments are shown in FIG. 23. As expected, insulin was able to significantly induce Akt3 activity (phosphorylation) in WM115 melanoma cells, while no signal was observed in MCF7 breast epithelial or LNCaP prostate cells.

Example 24 Reduction of Expression of Akt3

By identifying suitable shRNA sequences, for example as described in US2008014037, it is possible to knock down expression of Akt3 to different levels (e.g., 20%, 40%, 60%, 70%, 80%, 90%, 100%). Attempts to induce EMT in mammalian, preferably human, cells with different levels of Akt3 knockdown can be used to define the minimum degree of Akt3 knockdown required to prevent EMT, thus identifying the therapeutic window. Furthermore, by selecting a level of Akt3 knockdown that is just insufficient to prevent EMT, it is possible to generate a mammalian, preferably human, cell line that is particularly sensitive to inhibitors of EMT. In such a cell line there is only just enough Akt3 expression to allow EMT to occur, and compounds which inhibit Akt3 signalling even slightly will block EMT. Such cell lines are thus useful screening tools for inhibitors of EMT, and especially inhibitors of Akt3.

INDUSTRIAL APPLICATION

The invention is industrially applicable through operation of methods in accordance with the invention.

The invention claimed is:

1. A method of diagnosing and treating breast cancer comprising: (a) obtaining a sample from a subject; (b) detecting a level of epithelial-to-mesenchymal transition (EMT) in the sample from the subject by contacting the sample with a reagent that specifically binds Akt3 protein or Akt3 mRNA and detecting the expression level of Akt3 in the sample; (c) diagnosing the subject with increased risk of metastatic breast cancer when the level of EMT is increased in the sample as compared to a reference level; and (d) administering an effective amount of an Axl inhibitor to the subject diagnosed with increased risk of metastatic breast cancer.

2. The method of claim 1, wherein Akt3 mRNA is detected in step (b).

3. The method of claim 2, wherein Akt3 mRNA comprises an mRNA encoding the protein of SEQ ID NO: 1 or SEQ ID NO: 2.

4. The method of claim 1, wherein Akt3 protein is detected in step (b).

5. The method of claim 4, wherein Akt3 protein comprises SEQ ID NO: 1 or SEQ ID NO: 2.

6. The method of claim 1, wherein the Axl inhibitor comprises BGB324/R428.

7. The method of claim 1, wherein the sample is a breast tumour cell.

8. A method of treating breast cancer in a subject comprising: contacting a sample from the subject with a reagent that specifically binds Akt3 protein or Akt3 mRNA; detecting the expression level of Akt3 to determine the level of epithelial-to-mesenchymal transition (EMT) as compared to a reference level; and administering a therapeutically effective amount of an Axl inhibitor to the subject provided that a sample from the subject has an increased level of epithelial-to-mesenchymal transition (EMT) as compared to a reference level.

9. The method of claim 8, wherein Akt3 mRNA is contacted.

10. The method of claim 9, wherein Akt3 mRNA comprises an mRNA encoding the protein of SEQ ID NO: 1 or SEQ ID NO: 2.

11. The method of claim 8, wherein Akt3 protein is contacted.

12. The method of claim 11, wherein Akt3 protein comprises SEQ ID NO: 1 or SEQ ID NO: 2.

13. The method of claim 8, wherein the Axl inhibitor comprises BGB324/R428.

14. The method of claim 8, wherein the sample is a breast tumour cell.

* * * * *

```
                        SEQUENCE LISTING

<160> NUMBER OF SEQ ID NOS: 2

<210> SEQ ID NO 1
<211> LENGTH: 479
<212> TYPE: PRT
<213> ORGANISM: Homo sapiens

<400> SEQUENCE: 1

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
    130                 135                 140
```

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
            165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
        210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
                260                 265                 270

Lys Leu Glu Asn Leu Met Leu Asp Lys Asp Gly His Ile Lys Ile Thr
            275                 280                 285

Asp Phe Gly Leu Cys Lys Glu Gly Ile Thr Asp Ala Ala Thr Met Lys
290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
        370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
        450                 455                 460

Arg Pro His Phe Pro Gln Phe Ser Tyr Ser Ala Ser Gly Arg Glu
465                 470                 475

<210> SEQ ID NO 2
<211> LENGTH: 465
<212> TYPE: PRT
<213> ORGANISM: Homo sapiens

<400> SEQUENCE: 2

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

```
Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
                100                 105                 110

Glu Glu Glu Arg Met Asn Cys Ser Pro Thr Ser Gln Ile Asp Asn Ile
            115                 120                 125

Gly Glu Glu Glu Met Asp Ala Ser Thr Thr His His Lys Arg Lys Thr
            130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
                180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
                260                 265                 270

Lys Leu Glu Asn Leu Met Leu Asp Lys Asp Gly His Ile Lys Ile Thr
            275                 280                 285

Asp Phe Gly Leu Cys Lys Glu Gly Ile Thr Asp Ala Ala Thr Met Lys
            290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
                340                 345                 350

Lys Leu Phe Glu Leu Ile Leu Met Glu Asp Ile Lys Phe Pro Arg Thr
            355                 360                 365

Leu Ser Ser Asp Ala Lys Ser Leu Leu Ser Gly Leu Leu Ile Lys Asp
            370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
            435                 440                 445
```

```
Pro Glu Lys Cys Gln Gln Ser Asp Cys Gly Met Leu Gly Asn Trp Lys
    450                 455                 460
Lys
465
```